United States Patent
Bielas

(10) Patent No.: US 11,441,180 B2
(45) Date of Patent: *Sep. 13, 2022

(54) COMPOSITIONS AND METHODS FOR ACCURATELY IDENTIFYING MUTATIONS

(71) Applicant: Fred Hutchinson Cancer Research Center, Seattle, WA (US)

(72) Inventor: Jason H. Bielas, Seattle, WA (US)

(73) Assignee: Fred Hutchinson Cancer Center, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/091,676

(22) Filed: Nov. 6, 2020

(65) Prior Publication Data

US 2021/0054455 A1 Feb. 25, 2021

Related U.S. Application Data

(60) Continuation of application No. 16/898,155, filed on Jun. 10, 2020, now abandoned, which is a continuation of application No. 16/657,898, filed on Oct. 18, 2019, now abandoned, which is a continuation of application No. 16/121,559, filed on Sep. 4, 2018, now abandoned, which is a continuation of application No. 15/199,784, filed on Jun. 30, 2016, now Pat. No. 10,450,606, which is a division of application No. 14/378,870, filed as application No. PCT/US2013/026505 on Feb. 15, 2013, now Pat. No. 10,011,871.

(60) Provisional application No. 61/600,535, filed on Feb. 17, 2012.

(51) Int. Cl.
| | |
|---|---|
| *C12Q 1/6874* | (2018.01) |
| *C12Q 1/6869* | (2018.01) |
| *C12N 15/10* | (2006.01) |
| *C40B 50/06* | (2006.01) |
| *C12Q 1/6827* | (2018.01) |
| *C12N 15/70* | (2006.01) |
| *C12N 15/81* | (2006.01) |
| *C12N 15/85* | (2006.01) |
| *C40B 40/08* | (2006.01) |

(52) U.S. Cl.
CPC .......... *C12Q 1/6874* (2013.01); *C12N 15/10* (2013.01); *C12N 15/1065* (2013.01); *C12N 15/1093* (2013.01); *C12N 15/70* (2013.01); *C12N 15/81* (2013.01); *C12N 15/85* (2013.01); *C12Q 1/6827* (2013.01); *C12Q 1/6869* (2013.01); *C40B 40/08* (2013.01); *C40B 50/06* (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 5,308,751 A | 5/1994 | Ohkawa et al. |
| 6,013,445 A | 1/2000 | Albrecht et al. |
| 6,143,496 A | 11/2000 | Brown et al. |
| 6,404,907 B1 | 6/2002 | Gilchrist et al. |
| 6,818,395 B1 | 11/2004 | Quake et al. |
| 6,833,246 B2 | 12/2004 | Balasubramanian |
| 7,169,560 B2 | 1/2007 | Lapidus et al. |
| 7,264,929 B2 | 9/2007 | Rothberg et al. |
| 7,282,337 B1 | 10/2007 | Harris et al. |
| 7,537,897 B2 | 5/2009 | Brenner et al. |
| 7,666,593 B2 | 2/2010 | Lapidus |
| 7,700,286 B2 | 4/2010 | Stroun et al. |
| 7,754,429 B2 | 7/2010 | Rigatti et al. |
| 8,168,385 B2 | 5/2012 | Brenner et al. |
| 8,318,434 B2 | 11/2012 | Cuppens |
| 8,383,345 B2 | 2/2013 | Shendure et al. |
| 8,586,310 B2 | 11/2013 | Mitra et al. |
| 8,741,606 B2 | 6/2014 | Casbon et al. |
| 8,865,410 B2 | 10/2014 | Shendure et al. |
| 9,085,798 B2 | 7/2015 | Chee |
| 9,404,156 B2 | 8/2016 | Hicks et al. |
| 9,476,095 B2 | 10/2016 | Vogelstein et al. |
| 9,752,188 B2 | 9/2017 | Schmitt et al. |
| 10,011,871 B2 | 7/2018 | Bielas |
| 10,385,393 B2 * | 8/2019 | Salk et al. ........... C12Q 1/6806 |
| 10,450,606 B2 | 10/2019 | Bielas |
| 2002/0164629 A1 | 11/2002 | Quake et al. |
| 2005/0019776 A1 | 1/2005 | Callow et al. |

(Continued)

FOREIGN PATENT DOCUMENTS

| | | |
|---|---|---|
| DE | 102008025656 | 12/2009 |
| EP | 2828218 | 1/2015 |

(Continued)

OTHER PUBLICATIONS

Beck et al., "Next Generation Sequencing of Serum Circulating Nucleic Acids from Patients with Invasive Ductal Breast Cancer Reveals Differences to Healthy and Nonmalignant Controls," Mol. Cancer Res. 2010, 8:335-342. (Year: 2010).*

(Continued)

*Primary Examiner* — Kaijiang Zhang
(74) *Attorney, Agent, or Firm* — Greenberg Traurig, LLP

(57) ABSTRACT

The present disclosure provides compositions and methods for accurately detecting mutations by uniquely tagging double stranded nucleic acid molecules with dual cyphers such that sequence data obtained from a sense strand can be linked to sequence data obtained from an anti-sense strand when sequenced, for example, by massively parallel sequencing methods.

15 Claims, 6 Drawing Sheets

Specification includes a Sequence Listing.

(56) References Cited

U.S. PATENT DOCUMENTS

| | | |
|---|---|---|
| 2008/0261204 A1 | 10/2008 | Lexow |
| 2009/0026082 A1 | 1/2009 | Rothberg et al. |
| 2009/0099041 A1 | 4/2009 | Church et al. |
| 2009/0127589 A1 | 5/2009 | Rothberg et al. |
| 2009/0156412 A1 | 6/2009 | Harris et al. |
| 2009/0191565 A1 | 7/2009 | Lapidus et al. |
| 2009/0215633 A1 | 8/2009 | Eijk et al. |
| 2010/0035252 A1 | 2/2010 | Rothberg et al. |
| 2010/0041048 A1* | 2/2010 | Diehl et al. ......... C12Q 1/6886 435/6.16 |
| 2010/0137143 A1 | 6/2010 | Rothberg et al. |
| 2010/0188073 A1 | 7/2010 | Rothberg et al. |
| 2010/0197507 A1 | 8/2010 | Rothberg et al. |
| 2010/0227329 A1 | 9/2010 | Cuppens |
| 2010/0282617 A1 | 11/2010 | Rothberg et al. |
| 2010/0300559 A1 | 12/2010 | Schultz et al. |
| 2010/0300895 A1 | 12/2010 | Nobile et al. |
| 2010/0301398 A1 | 12/2010 | Rothberg et al. |
| 2010/0304982 A1 | 12/2010 | Hinz et al. |
| 2012/0058468 A1 | 3/2012 | McKeown |
| 2012/0283110 A1 | 11/2012 | Shendure et al. |
| 2013/0005585 A1 | 1/2013 | Anderson |
| 2014/0155274 A1 | 6/2014 | Xie et al. |
| 2015/0044687 A1 | 2/2015 | Schmitt et al. |
| 2015/0087535 A1 | 3/2015 | Patel |
| 2015/0197798 A1 | 7/2015 | Xu et al. |
| 2015/0368708 A1 | 12/2015 | Talasaz |
| 2015/0376608 A1 | 12/2015 | Kaper et al. |
| 2016/0040229 A1 | 2/2016 | Talasaz et al. |
| 2016/0046986 A1 | 2/2016 | Eltoukhy et al. |
| 2016/0251704 A1 | 9/2016 | Talasaz et al. |
| 2016/0304948 A1 | 10/2016 | Lee et al. |
| 2016/0319345 A1 | 11/2016 | Gnerre et al. |
| 2016/0326578 A1 | 11/2016 | Bielas |
| 2017/0136433 A1 | 5/2017 | Sun et al. |
| 2018/0044731 A1 | 2/2018 | Valouev et al. |
| 2018/0363048 A1 | 12/2018 | Bielas |
| 2018/0363049 A1 | 12/2018 | Bielas |
| 2020/0048706 A1 | 2/2020 | Bielas |
| 2020/0048707 A1 | 2/2020 | Bielas |
| 2020/0299766 A1 | 9/2020 | Bielas |
| 2020/0299767 A1 | 9/2020 | Bielas |
| 2020/0385804 A1 | 12/2020 | Bielas |
| 2021/0222243 A1 | 7/2021 | Bielas |
| 2021/0238676 A1 | 8/2021 | Bielas |
| 2021/0238678 A1 | 8/2021 | Bielas |
| 2021/0246504 A1 | 8/2021 | Bielas |
| 2021/0317525 A1 | 10/2021 | Bielas |
| 2021/0317526 A1 | 10/2021 | Bielas |
| 2021/0340619 A1 | 11/2021 | Bielas |
| 2021/0388435 A1 | 12/2021 | Bielas |
| 2021/0395818 A1 | 12/2021 | Bielas |

FOREIGN PATENT DOCUMENTS

| | | |
|---|---|---|
| EP | 2814959 B1 | 1/2018 |
| JP | 4747245 | 8/2011 |
| WO | WO-93/06239 A1 | 4/1993 |
| WO | 96/12039 | 4/1996 |
| WO | 98/44151 | 10/1998 |
| WO | 00/18957 | 4/2000 |
| WO | 00/60124 | 10/2000 |
| WO | 2004/003136 | 1/2004 |
| WO | 2004065562 A2 | 8/2004 |
| WO | WO-2004/081183 A2 | 9/2004 |
| WO | WO-2004/081183 A3 | 9/2004 |
| WO | 2005/042759 | 5/2005 |
| WO | 2005/063980 | 7/2005 |
| WO | 2005/068656 | 7/2005 |
| WO | 2006/084130 | 8/2006 |
| WO | 2006/137733 | 12/2006 |
| WO | 2007/037678 | 4/2007 |
| WO | 2007/073165 | 6/2007 |
| WO | 2007/073171 | 6/2007 |
| WO | 2007/106509 | 9/2007 |
| WO | 2007/114693 | 10/2007 |
| WO | 2008093098 A2 | 8/2008 |
| WO | 2009/036525 | 3/2009 |
| WO | 2009/152928 | 12/2009 |
| WO | 2010/115100 | 10/2010 |
| WO | 2010/115154 | 10/2010 |
| WO | 2010/126614 | 11/2010 |
| WO | 2010/127186 A1 | 11/2010 |
| WO | 2011/155833 | 12/2011 |
| WO | 2012/038839 | 3/2012 |
| WO | 2012/106546 | 8/2012 |
| WO | 2012/142213 | 10/2012 |
| WO | 2012/148477 | 11/2012 |
| WO | 2013/123442 | 8/2013 |
| WO | 2013/142389 | 9/2013 |
| WO | 2013138510 A1 | 9/2013 |
| WO | 2013/181170 | 12/2013 |
| WO | 2015/094861 | 6/2015 |
| WO | 2015/200609 | 12/2015 |
| WO | 2016/176091 | 11/2016 |
| WO | 2017/040306 | 3/2017 |
| WO | 2017/100441 | 6/2017 |
| WO | 2017/218512 | 12/2017 |
| WO | 2018/031760 | 2/2018 |
| WO | 2018/031929 | 2/2018 |

OTHER PUBLICATIONS

"English translation of", D2 (DE 10 2008 025656).
"European Examination Report", EP Application No. 18150361.6, dated Apr. 12, 2019, 4 pages.
"European Summons to Attend Oral Proceedings Pursuant to Rule 115(1) EPC, and Provisional Opinion", EP Patent Application No. 13706397.0, dated Aug. 6, 2019, 10 pages.
"European Third Party Observations", EP Application No. 18150361. 6, dated Mar. 18, 2019, 22 pages.
"Extended European Search Report", EP Application No. 18150361.6, dated Jun. 13, 2018.
"Notice of Oppostion", EP Patent 2,814,959 and Arguments in Support of Same, dated Oct. 2018, 21 pages.
Bainbridge, et al., "Whole exome capture in solution with 3 Gbp of data", Genome Biology 11: R62, 2010.
Baird, et al., "Rapid SNP Discovery and Genetic Mapping Using Sequenced RAD markers", PLOS One, 3(10):e3376, 2008, 1-7.
Bettegowda, et al., "Detection of circulating tumor DNA in early- and late-stage human malignancies", SciTrans Med, vol. 6. No. 224, 2014, 1-11.
Bielas, et al., "Human cancers express a mutator phenotype", Proc. Natl. Acad. Sci. USA 103(48), Nov. 28, 2006, 18238-18242.
Bielas, et al., "Quantification of random genomic mutations", Nature Methods 2(4), 2005., 285-290.
Bowtell, "The genesis and evolution of high-grade serous ovarian cancer", Nat. Rev. Cancer 10(11), Nov. 2010, 803-808.
Brandon, et al., "Mitochondrial mutations in cancer", Oncogene 25(34), 2006, 4647-4662.
Braslavsky, et al., "Sequence information can be obtained from single DNA molecules", PNAS, vol. 100, No. 7, 2003, 3960-3964.
Brockman, et al., "Quality scores and SNP detection in sequencing-by-synthesis systems", Methods, 18, 2008, 763-770.
Cancer Genome Atlas Research Net, "Integrated Genomic Analyses of Ovarian Carcinoma", Nature 474(7353), 2011, 609-615.
Casbon, et al., "A method for counting PCR template molecules with application to next-generation sequencing", Nucleic Acids Res. 39(12), 2011, e81.
Chatterjee, et al., "Mitochondrial DNA mutations in human cancer", Oncogene 25(34), 2006, 4663-4674.
Chmielecki, et al., "Targeted next-generation sequencing of DNA regions proximal to a conserved GXGXXG signaling motif enables systematic discovery of tyrosine kinase fusions in cancer", Nucleic Acids Research, vol. 38, No. 20, 2010, 6985-6996.
Copeland, et al., "Mitochondrial DNA Alterations in Cancer", Cancer Invest. 20(4), 2002, 557-569.

(56) References Cited

OTHER PUBLICATIONS

Duncavage, et al., "Hybrid Capture and Next-Generation Sequencing Identify Viral Integration Sites from Formalin-Fixed, Paraffin-Embedded Tissue", J Mol Diagn., vol. 13, No. 3, 2011, 325-333.
Fleishmann, et al., "Whole-genome random sequencing and assembly of Haemophilus influenzae Rd", Science, vol. 269, issue 5223, 1995, 496-512.
Fullwood, et al., "Next-generation DNA sequencing of paired-end tags (PET) for transcriptome and genome analyses", Genome Res, 19, 2009, 521-532.
Harris, et al., "Single-Molecule DNA Sequencing of a Viral Genome", Science, vol. 320, 2008, 106-109.
Hashimoto, et al., "5'-end SAGE for the analysis of transcriptional start sites", Nature Biotechnology, 22, 2004, 1146-1149.
Hiatt, et al., "Parallel, tag-directed assembly of locally derived short sequence reads", Nature Methods, 7(2), 2010, 119-122.
Homer, et al., "Improved variant discovery through local re-alignment of short-read next generation sequencing data using SRMA", Genome Biology, 11:R99, 2010.
Hug, et al., "Measurement of the Number of Molecules of a Single mRNA Species in a Complex mRNA Preparation", J. theor. Biol. 221(4), 2003, 615-624.
Huse, et al., "Accuracy and quality of massively parallel DNA pyrosequencing", Genome Biology, 8:RI43, 2007.
ILLUMINA, "Data Sheet: Sequencing."
Jabara, et al., "Accurate sampling and deep sequencing of the HIV-1 protease gene using a Primer ID", Proc Natil Acad Sci USA 108(50), 2011, 20166-20171.
Jones, et al., "Comparative lesion sequencing provides insights into tumor evolution", Proc. Natl. Acad. Sci. USA 105(11), Mar. 18, 2008, 4283-4288.
Kinde, et al., "Detection and quantification of rare mutations with massively parallel sequencing", Proc. Natl. Acad. Sci. USA 108(23), Jun. 7, 2011, 9530-9535.
Kivioja, et al., "Counting absolute numbers of molecules using unique molecular identifiers", Nat Methods, 9(1), 2011, 72-4.
Korbel, et al., "Paired-End Mapping Reveals Extensive Structural Variation in the Human Genome", Science, 318(5849), 2007, 420-426.
Kou, et al., "Benefits and Challenges with Applying Unique Molecular Identifiers in Next Generation Sequencing to Detect Low Frequency Mutations", PLoS One, 11(1):e0146638, 2016.
Kraytsberg, et al., "Single molecule PCR in mtDNA mutational analysis: genuine mutations vs. damage bypass-derived artifacts", Methods 46(4), 2008, 269-273.
Li, et al., "A new approach for detecting low-level mutations in next-generation sequence data", Genome Biology, 13:R34, 2012.
Linnarsson, "Recent advances in DNA sequencing methods—general principles of sample preparaton", Experimental Cell Research, 316, 2010, 1339-1343.
Mardis, et al., "The impact of next-generation sequencing technology on genetics", Trends Genet 24(3), 2008, 133-141.
Marguiles, et al., "Genome sequencing in microfabricated high-density picolitre reactors", Nature 437(7057), 2005, 376-380.
Maxam, et al., "A new method for sequencing DNA", PNAS, vol. 74, No. 2, 1977, 560-564.
McCloskey, et al., "Encoding PCR products with batch-stamps and barcodes", Biochem Genet. 45(11-12), 2007, 761-767.
Metzker, "Sequencing technologies—the next generation", Nature Reviews Genetics, 11, 2010, 31-46.
Moudrianakis, et al., "Base Sequence Determination In Nucleic Acids With The Electron Microscope III. chemistry and microscopy of guanine-labeled DNA", PNAS, vol. 53, No. 3, 1965, 564-671.
Mouliere, et al., "Circulating tumor-derived DNA is shorter than somatic DNA in plasma", PNAS, vol. 112, No. 11, 2015, 3178-3179.
Mouliere, et al., "Multi-marker Analysis of Circulatig Cell-free DNA Toward Personalized Medicine for Colorectal Cancer", Mol Oncol., vol. 8, No. 5, Mar. 2014, 927-947.

Newman, et al., "An ultrasensitive method for quantitating circulating tumor DNA with broad patient coverage", Nat Med, vol. 20, No. 5, 2014, 548-554.
Ng, et al., "Gene identification signature (GIS) analysis for transcriptome characterization and genome annotation", Nature Methods, 2(2), 2005, 105-111.
Ng, et al., "Multiplex sequencing of paired-end ditags (MS-PET): a strategy for the ultra-high-throughput analysis of transcriptomes and genomes", NAR, 34(12), 2006, e84.
Niedringhaus, et al., "Landscape of Next-Generation Sequencing Technologies", Anal. Chem. 83(12), 2011, 4327-4341.
Saha, et al., "Using the transcriptome to annotate the genome", Nature Biotechnology, 20, 2002, 508-512.
Sanger, et al., "DNA sequencing with chain-terminating inhibitors", PNAS, vol. 74, No. 12, 1977, 5463-5467.
Schmitt, et al., "Detection of ultra-rare mutations by next-generation sequencing", PNAS, vol. 109, No. 36, 2012, 14508-14513.
Shiroguchi, et al., "Digital RNA Sequencing Minimizes Sequence-dependent Bias and Amplification Noise with Optimized Single-molecule Barcodes", PNAS 109(4), 2012, 1347-1352.
Soni, et al., "Progress toward ultrafast DNA sequencing using solid-state nanopores", Clin. Chem, 53(11), 2007, 1996-2001.
Srivatsan, et al., "High-Precision, Whole-Genome Sequencing of Laboratory Strains Facilitates Genetic Studies", PLoS Genet, 4(8) e1000139, 2008.
Taylor, et al., "Mitochondrial DNA mutations in human disease", Nat. Rev. Genet. 6(5), May 2005, 389-402.
Travers, et al., "A flexible and efficient template format for circular consensus sequencing and SNP detection", NAR, 38 (15), Aug. 1, 2010, 1-8.
Varley, et al., "Bisulfite Patch PCR enables multiplexed sequencing of promoter methylation across cancer samples", Genome Research, 20, 2010, 1279-87.
Velculescu, et al., "Serial analysis of gene expression", Science, vol. 270, No. 5235, 1995, 484-487.
Walsh, et al., "Detection of inherited mutations for breast and ovarian cancer using genomic capture and massively parallel sequencing", PNAS, vol. 107, No. 28, 2010, 12629-12633.
Wei, et al., "5' Long serial analysis of gene expression (LongSAGE) and 3' LongSAGE for transcriptome characterization and genome annotation", PNAS, vol. 101, No. 32, 2004, 11701-11706.
Zhang, et al., "The impact of next-generation sequencing on genomics", J Genet Genomics, 38(3), 2011, 95-109.
Zheng, et al., "Origins of human mitochondrial point mutations as DNA poly m erase y-mediated errors", Mutat. Res. 599(1-2), 2006, 11-20.
Zilberman, et al., "Genome-wide analysis of DNA methylation patterns", Development 134, doi:10.1242/dev.001131, 2007, 3959-3965.
Rhoads, A. et al. (Oct. 2015, e-published Nov. 2, 2015). "PacBio Sequencing and Its Applications," *Genomics Proteomics Bioinformatics* 13(5):278-289.
Thompson, J.F. et al. (Oct. 2010). "Single molecule sequencing with a HeliScope genetic analysis system," *Current Protocols in Molecular Biology* Chapter 7:Unit7.10.
Extended European Search Report dated Jun. 28, 2021, for EP Patent Application No. 20215829.1, 9 pages.
Meldrum, C. et al. (Nov. 2011). "Next-generation sequencing for cancer diagnostics: a practical perspective," *Clin Biochem Rev* 32(4):177-195.
Myllykangas, S. et al. (Dec. 14, 2011). "Targeted sequencing library preparation by genomic DNA circularization," *BMC Biotechnol* 11:122.
Beck, J. et al. (Mar. 2010, e-published Mar. 9, 2010). "Next generation sequencing of serum circulating nucleic acids from patients with invasive ductal breast cancer reveals differences to healthy and nonmalignant controls." Mol Cancer Res 8(3):335-342.
Bentley et al., "Accurate whole human genome sequencing using reversible terminator chemistry", nature, Nov. 6, 2008, vol. 456, pp. 53-59.
UMass Chan Medical School, Lab Guidance Note, Obtainable from the following web address: https://www.umassmed.edu/contentassets/

(56) References Cited

OTHER PUBLICATIONS

5ea3699998c442bb8c9b1a3cf95dbb24/indexing-and-barcoding-for-illumina-nextgen-sequencing.pdf.

Kaur et al., "Novel amplification of DNA in a hairpin structure: towards a radical elimination of PCR errors from amplified DNA", Nucleic Acids Research, Jan. 16, 2003, vol. 31, No. 6, pp. 1-7.

Kircher et al., "Double indexing overcomes inaccuracies in multiplex sequencing on the Illumina platform", Nucleic Acids Research, Oct. 21, 2011, vol. 40, No. 1, pp. 1-8.

Son et al., "Preparing DNA Libraries for Multiplexed Paired-End Deep Sequencing for Illumina GA Sequencers", Current Protocols in Microbiology.

Supporting Information from Kinde , et al. , "Detection and quantification of rare mutations with massively parallel sequencing", Proc. Natl. Acad. Sci. USA 108(23), Jun. 7, 2011, 9530-9535.

Milbury et al., "PPCR-Based Methods for the Enrichment of Minority Alleles and Mutations" Clinical Chemistry, 2009, vol. 55, No. 4, pp. 632-640.

\* cited by examiner

COMPOSITIONS AND METHODS FOR ACCURATELY IDENTIFYING MUTATIONS

CROSS REFERENCE TO RELATED APPLICATION

This application claims the benefit of U.S. provisional patent application Ser. No. 61/600,535, filed Feb. 17, 2012, which is incorporated herein by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing 360056_409WO_SEQUENCE_LISTING_.txt. The text file is 4 KB, was created on Feb. 14, 2013, and is being submitted electronically via EFS-Web.

BACKGROUND

1. Technical Field

The present disclosure relates to compositions and methods for accurately detecting mutations using sequencing and, more particularly, uniquely tagging double stranded nucleic acid molecules such that sequence data obtained for a sense strand can be linked to sequence data obtained from the anti-sense strand when obtained via massively parallel sequencing methods.

2. Description of Related Art

Detection of spontaneous mutations (e.g., substitutions, insertions, deletions, duplications), or even induced mutations, that occur randomly throughout a genome can be challenging because these mutational events are rare and may exist in one or only a few copies of DNA. The most direct way to detect mutations is by sequencing, but the available sequencing methods are not sensitive enough to detect rare mutations. For example, mutations that arise de novo in mitochondrial DNA (mtDNA) will generally only be present in a single copy of mtDNA, which means these mutations are not easily found since a mutation must be present in as much as 10-25% of a population of molecules to be detected by sequencing (Jones et al., *Proc. Nat'l. Acad. Sci. U.S.A.* 105:4283-88, 2008). As another example, the spontaneous somatic mutation frequency in genomic DNA has been estimated to be as low as $1\times10^{-8}$ and $2.1\times10^{-6}$ in human normal and cancerous tissues, respectively (Bielas et al., *Proc. Nat'l Acad. Sci. U.S.A.* 10.3:18238-42, 2008).

One improvement in sequencing has been to take individual DNA molecules and amplify the number of each molecule by, for example, polymerase chain reaction (PCR) and digital PCR. Indeed, massively parallel sequencing represents a particularly powerful form of digital PCR because multiple millions of template DNA molecules can be analyzed one by one. However, the amplification of single DNA molecules prior to or during sequencing by PCR and/or bridge amplification suffers from the inherent error rate of polymerases employed for amplification, and spurious mutations generated during amplification may be mis-identified as spontaneous mutations from the original (endogenous unamplified) nucleic acid. Similarly, DNA templates damaged during preparation (ex vivo) may be amplified and incorrectly scored as mutations by massively parallel sequencing techniques. Again, using mtDNA as an example, experimentally determined mutation frequencies are strongly dependent on the accuracy of the particular assay being used (Kraytsberg et al., *Methods* 46:269-73, 2008)—these discrepancies suggest that the spontaneous mutation frequency of mtDNA is either below, or very close to, the detection limit of these technologies. Massively parallel sequencing cannot generally be used to detect rare variants because of the high error rate associated with the sequencing process—one process using bridge amplification and sequencing by synthesis has shown an error rate that varies from about 0.06% to 1%, which depends on various factors including read length, base-calling algorithms, and the type of variants detected (see Kinde et al., *Proc. Nat'l. Acad. Sci. U.S.A.* 108:9530-5, 2011).

BRIEF SUMMARY

In one aspect, the present disclosure provides a double-stranded nucleic acid molecule library that includes a plurality of target nucleic acid molecules and a plurality of random cyphers, wherein the nucleic acid library comprises molecules having a formula of $X^a$—$X^b$—Y, $X^b$—$X^a$—Y, Y—$X^a$—$X^b$, Y—$X^b$—X, $X^a$—Y—$X^b$, or $X^b$—Y—$X^a$ (in 5' to 3' order), wherein (a) $X^a$ comprises a first random cypher, (b) Y comprises a target nucleic acid molecule, and (c) $X^b$ comprises a second random cypher. Furthermore, each of the plurality of random cyphers comprise a length ranging from about 5 nucleotides to about 50 nucleotides (or about 5 nucleotides to about 10 nucleotides, or a length of about 6, about 7, about 8, about 9, about 10, about 11, about 12, about 13, about 14, about 15, about 16, about 17, about 18, about 19, or about 20 nucleotides).

In certain embodiments, the double-stranded sequences of the $X^a$ and $X^b$ cyphers are the same (e.g., $X^a$=$X^b$) for one or more target nucleic acid molecules, provided that each such target nucleic acid molecule does not have the same double-stranded cypher sequence as any other such target nucleic acid molecule. In certain other embodiments, the double-stranded sequence of the $X^a$ cypher for each target nucleic acid molecule is different from the double-stranded sequence of the $X^b$ cypher. In further embodiments, the double-stranded nucleic acid library is contained in a self-replicating vector, such as a plasmid, cosmid, YAC, or viral vector.

In a further aspect, the present disclosure provides a method for obtaining a nucleic acid sequence or accurately detecting a true mutation in a nucleic acid molecule by amplifying each strand of the aforementioned double-stranded nucleic acid library wherein a plurality of target nucleic acid molecules and plurality of random cyphers are amplified, and sequencing each strand of the plurality of target nucleic acid molecules and plurality of random cyphers. In certain embodiments, the sequencing is performed using massively parallel sequencing methods. In certain embodiments, the sequence of one strand of a target nucleic acid molecule associated with the first random cypher aligned with the sequence of the complementary strand associated with the second random cypher results in a measureable sequencing error rate ranging from about $10^{-6}$ to about $10^{-8}$.

DETAILED DESCRIPTION

Figure 1:
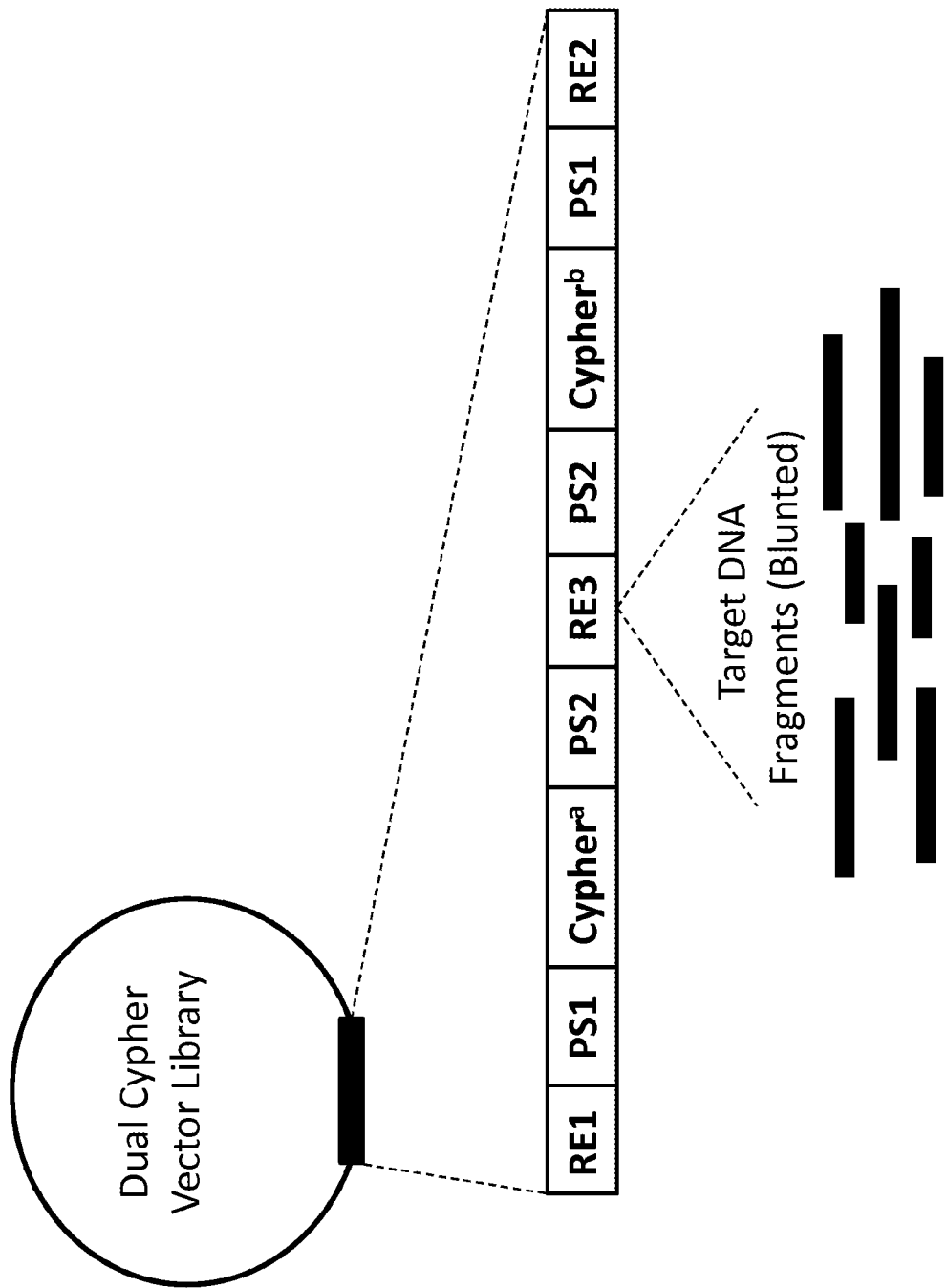
FIG. 1 is a cartoon illustration of an exemplary vector of the present disclosure useful for generating a double-stranded nucleic acid library.

In one aspect, the present disclosure provides a double-stranded nucleic acid library wherein target nucleic acid molecules include dual cyphers (i.e., barcodes or origin identifier tags), one on each end (same or different), so that sequencing each complementary strand can be connected or linked back to the original molecule. The unique cypher on each strand links each strand with its original complementary strand (e.g., before any amplification), so that each paired sequence serves as its own internal control. In other words, by uniquely tagging double-stranded nucleic acid molecules, sequence data obtained from one strand of a single nucleic acid molecule can be specifically linked to sequence data obtained from the complementary strand of that same double-stranded nucleic acid molecule. Furthermore, sequence data obtained from one end of a double-stranded target nucleic acid molecule can be specifically linked to sequence data obtained from the opposite end of that same double-stranded target nucleic acid molecule (if, for example, it is not possible to obtain sequence data across the entire target nucleic acid molecule fragment of the library).

The compositions and methods of this disclosure allow a person of ordinary skill in the art to more accurately distinguish true mutations (i.e., naturally arising in vivo mutations) of a nucleic acid molecule from artifact "mutations" (i.e., ex vivo mutations or errors) of a nucleic acid molecule that may arise for various reasons, such as a downstream amplification error, a sequencing error, or physical or chemical damage. For example, if a mutation pre-existed in the original double-stranded nucleic acid molecule before isolation, amplification or sequencing, then a transition mutation of adenine (A) to guanine (G) identified on one strand will be complemented with a thymine (T) to cysteine (C) transition on the other strand. In contrast, artifact "mutations" that arise later on an individual (separate) DNA strand due to polymerase errors during isolation, amplification or sequencing are extremely unlikely to have a matched base change in the complementary strand. The approach of this disclosure provides compositions and methods for distinguishing systematic errors (e.g., polymerase read fidelity errors) and biological errors (e.g., chemical or other damage) from actual known or newly identified true mutations or single nucleotide polymorphisms (SNPs).

In certain embodiments, the two cyphers on each target molecule have sequences that are distinct from each other and, therefore, provide a unique pair of identifiers wherein one cypher identifies (or is associated with) a first end of a target nucleic acid molecule and the second cypher identifies (or is associated with) the other end of the target nucleic acid molecule. In certain other embodiments, the two cyphers on each target molecule have the same sequence and, therefore, provide a unique identifier for each strand of the target nucleic acid molecule. Each strand of the double-stranded nucleic acid library (e.g., genomic DNA, cDNA) can be amplified and sequenced using, for example, next generation sequencing technologies (such as, emulsion PCR or bridge amplification combined with pyrosequencing or sequencing by synthesis, or the like). The sequence information from each complementary strand of a first double-stranded nucleic acid molecule can be linked and compared (e.g., computationally "de-convoluted") due to the unique cyphers associated with each end or strand of that particular double-stranded nucleic acid molecule. In other words, each original double-stranded nucleic acid molecule fragment found in a library of molecules can be individually reconstructed due to the presence of an associated unique barcode or pair of barcode (identifier tag) sequences on each target fragment or strand.

By way of background, any spontaneous or induced mutation will be present in both strands of a native genomic, double-stranded DNA molecule. Hence, such a mutant DNA template amplified using PCR will result in a PCR product in which 100% of the molecules produced by PCR include the mutation. In contrast to an original, spontaneous mutation, a change due to polymerase error will only appear in one strand of the initial template DNA molecule (while the other strand will not have the artifact mutation). If all DNA strands in a PCR reaction are copied equally efficiently, then any polymerase error that emerges from the first PCR cycle likely will be found in at least 25% of the total PCR product. But DNA molecules or strands are not copied equally efficiently, so DNA sequences amplified from the strand that incorporated an erroneous nucleotide base during the initial amplification might constitute more or less than 25% of the population of amplified DNA sequences depending on the efficiency of amplification, but still far less than 100%. Similarly, any polymerase error that occurs in later PCR cycles will generally represent an even smaller proportion of PCR products (i.e., 12.5% for the second cycle, 6.25% for the third, etc.) containing a "mutation." PCR-induced mutations may be due to polymerase errors or due to the polymerase bypassing damaged nucleotides, thereby resulting in an error (see, e.g., Bielas and Loeb, *Nat. Methods* 2:285-90, 2005). For example, a common change to DNA is the deamination of cytosine, which is recognized by Taq polymerase as a uracil and results in a cytosine to thymine transition mutation (Zheng et al., *Mutat. Res.* 599:11-20, 2006)—that is, an alteration in the original DNA sequence may be detected when the damaged DNA is sequenced, but such a change may or may not be recognized as a sequencing reaction error or due to damage arising ex vivo (e.g., during or after nucleic acid isolation).

Due to potential artifacts and alterations of nucleic acid molecules arising from isolation, amplification and sequencing, the accurate identification of true somatic DNA mutations is difficult when sequencing amplified nucleic acid molecules.

Consequently, evaluation of whether certain mutations are related to, or are a biomarker for, various disease states (e.g., cancer) or aging becomes confounded.

Next generation sequencing has opened the door to sequencing multiple copies of an amplified single nucleic acid molecule—referred to as deep sequencing. The thought on deep sequencing is that if a particular nucleotide of a nucleic acid molecule is sequenced multiple times, then one can more easily identify rare sequence variants or mutations. In fact, however, the amplification and sequencing process has an inherent error rate (which may vary depending on DNA quality, purity, concentration (e.g., cluster density), or other conditions), so no matter how few or how many times a nucleic acid molecule is sequenced, a person of skill in the art cannot distinguish a polymerase error artifact from a true mutation (especially rare mutations).

While being able to sequence many different DNA molecules collectively is advantageous in terms of cost and time, the price for this efficiency and convenience is that various PCR errors complicate mutational analysis as long as their frequency is comparable to that of mutations arising in vivo—in other words, genuine in vivo mutations will be essentially indistinguishable from changes that are artifacts of PCR or sequencing errors.

Thus, the present disclosure, in a further aspect, provides methods for identifying mutations present before amplification or sequencing of a double-stranded nucleic acid library wherein the target molecules include a single double-stranded cypher or dual cyphers (i.e., barcodes or identifier tags), one on each end, so that sequencing each complementary strand can be connected back to the original molecule. In certain embodiments, the method enhances the sensitivity of the sequencing method such that the error rate is $5 \times 10^{-6}$, $10^{-6}$, $5 \times 10^{-7}$, $5 \times 10^{-8}$, $10^{-8}$ or less when sequencing many different target nucleic acid molecules simultaneously or such that the error rate is $5 \times 10^{-7}$, $10^{-7}$, $5 \times 10^{-4}$, $10^{-8}$ or less when sequencing a single target nucleic acid molecule in depth.

Prior to setting forth this disclosure in more detail, it may be helpful to an understanding thereof to provide definitions of certain terms to be used herein. Additional definitions are set forth throughout this disclosure.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the terms "about" and "consisting essentially of" mean±20% of the indicated range, value, or structure, unless otherwise indicated. It should be understood that the terms "a" and "an" as used herein refer to "one or more" of the enumerated components. The use of the alternative (e.g., "or") should be understood to mean either one, both, or any combination thereof of the alternatives. As used herein, the terms "include," "have" and "comprise" are used synonymously, which terms and variants thereof are intended to be construed as non-limiting.

As used herein, the term "random cypher" or "cypher" or "barcode" or "identifier tag" and variants thereof are used interchangeably and refer to a nucleic acid molecule having a length ranging from about 5 to about 50 nucleotides. In certain embodiments, all of the nucleotides of the cypher are not identical (i.e., comprise at least two different nucleotides) and optionally do not contain three contiguous nucleotides that are identical. In further embodiments, the cypher is comprised of about to about 15 nucleotides, about 6 to about 10 nucleotides, and preferably about 7 to about 12 nucleotides. Cyphers will generally be located at one or both ends a target molecule may, which may be incorporated directly onto target molecules of interest or onto a vector into which target molecules will be later added.

As used herein, "target nucleic acid molecules" and variants thereof refer to a plurality of double-stranded nucleic acid molecules that may be fragments or shorter molecules generated from longer nucleic acid molecules, including from natural samples (e.g., a genome), or the target nucleic acid molecules may be synthetic (e.g., cDNA), recombinant, or a combination thereof. Target nucleic acid fragments from longer molecules may be generated using a variety of techniques known in the art, such as mechanical shearing or specific cleavage with restriction endonucleases.

As used herein, a "nucleic acid molecule library" and variants thereof refers to a collection of nucleic acid molecules or fragments. In certain embodiments, the collection of nucleic acid molecules or fragments is incorporated into a vector, which can be transformed or transfected into an appropriate host cell. The target nucleic acid molecules of this disclosure may be introduced into a variety of different vector backbones (such as plasmids, cosmids, viral vectors, or the like) so that recombinant production of a nucleic acid molecule library can be maintained in a host cell of choice (such as bacteria, yeast, mammalian cells, or the like).

For example, a collection of nucleic acid molecules representing the entire genome is called a genomic library and a collection of DNA copies of messenger RNA is referred to as a complimentary DNA (cDNA) library. Methods for introducing nucleic acid molecule libraries into vectors are well known in the art (see, e.g., Current Protocols in Molecular Biology, Ausubel et al., Eds., Greene Publishing and Wiley-Interscience, New York, 1995; Sambrook et al., Molecular Cloning: A Laboratory Manual, 2nd Ed., Cold Spring Harbor Laboratory Vols. 1-3, 1989; Methods in Enzymology, Vol. 152, Guide to Molecular Cloning Techniques, Berger and Kimmel, Eds., San Diego: Academic Press, Inc., 1987).

Depending on the type of library to be generated, the ends of the target nucleic acid fragments may have overhangs or may be "polished" (i.e., blunted). Together, the target nucleic acid molecule fragments can be, for example, cloned directly into a cypher vector to generate a vector library, or be ligated with adapters to generate, for example, polonies. The target nucleic acid molecules, which are the nucleic acid molecules of interest for amplification and sequencing, may range in size from a few nucleotides (e.g., 50) to many thousands (e.g., 10,000). Preferably, the target fragments in the library range in size from about 100 nucleotides to about 750 nucleotides or about 1,000 nucleotides, or from about 150 nucleotides to about 250 nucleotides or about 500 nucleotides.

As used herein, a "nucleic acid molecule priming site" or "PS" and variants thereof are short, known nucleic acid sequences contained in the vector. A PS sequence can vary in length from 5 nucleotides to about 50 nucleotides in length, about 10 nucleotides to about 30 nucleotides, and preferably are about 15 nucleotides to about 20 nucleotides in length. In certain embodiments, a PS sequence may be included at the one or both ends or be an integral part of the random cypher nucleic acid molecules, or be included at the one or both ends or be an integral part of an adapter sequence, or be included as part of the vector. A nucleic acid molecule primer that is complementary to a PS included in a library of the present disclosure can be used to initiate a sequencing reaction.

For example, if a random cypher only has a PS upstream (5') of the cypher, then a primer complementary to the PS can be used to prime a sequencing reaction to obtain the sequence of the random cypher and some sequence of a target nucleic acid molecule cloned downstream of the cypher. In another example, if a random cypher has a first PS upstream (5') and a second PS downstream (3') of the cypher, then a primer complementary to the first PS can be used to prime a sequencing reaction to obtain the sequence of the random cypher, the second PS and some sequence of a target nucleic acid molecule cloned downstream of the second PS. In contrast, a primer complementary to the second PS can be used to prime a sequencing reaction to directly obtain the sequence of the target nucleic acid molecule cloned downstream of the second PS. In this latter case, more target molecule sequence information will be obtained since the sequencing reaction beginning from the second PS can extend further into the target molecule than does the reaction having to extend through both the cypher and the target molecule.

As used herein, "next generation sequencing" refers to high-throughput sequencing methods that allow the sequencing of thousands or millions of molecules in parallel. Examples of next generation sequencing methods include sequencing by synthesis, sequencing by ligation, sequencing by hybridization, polony sequencing, and pyrosequencing. By attaching primers to a solid substrate and a complementary sequence to a nucleic acid molecule, a nucleic acid molecule can be hybridized to the solid substrate via the primer and then multiple copies can be generated in a discrete area on the solid substrate by using polymerase to amplify (these groupings are sometimes referred to as polymerase colonies or polonies). Consequently, during the sequencing process, a nucleotide at a particular position can be sequenced multiple times (e.g., hundreds or thousands of times)—this depth of coverage is referred to as "deep sequencing."

As used herein, "base calling" refers to the computational conversion of raw or processed data from a sequencing instrument into quality scores and then actual sequences. For example, many of the sequencing platforms use optical detection and charge coupled device (CCD) cameras to generate images of intensity information (i.e., intensity information indicates which nucleotide is in which position of a nucleic acid molecule), so base calling generally refers to the computational image analysis that converts intensity data into sequences and quality scores. Another example is the ion torrent sequencing technology, which employs a proprietary semiconductor ion sensing technology to detect release of hydrogen ions during incorporation of nucleotide bases in sequencing reactions that take place in a high density array of micro-machined wells. There are other examples of methods known in the art that may be employed for simultaneous sequencing of large numbers of nucleotide molecules. Various base calling methods are described in, for example, Niedringhaus et al. (*Anal. Chem.* 83:4327, 2011), which methods are herein incorporated by reference in their entirety.

In the following description, certain specific details are set forth in order to provide a thorough understanding of various embodiments of this disclosure. However, upon reviewing this disclosure, one skilled in the art will understand that the invention may be practiced without many of these details. In other instances, newly emerging next generation sequencing technologies, as well as well-known or widely available next generation sequencing methods (e.g., chain-termination sequencing, dye-terminator sequencing, reversible dye-terminator sequencing, sequencing by synthesis, sequencing by ligation, sequencing by hybridization, polony sequencing, pyrosequencing, ion semiconductor sequencing, nanoball sequencing, nanopore sequencing, single molecule sequencing, FRET sequencing, base-heavy sequencing, and microfluidic sequencing), have not all been described in detail to avoid unnecessarily obscuring the descriptions of the embodiments of the present disclosure. Descriptions of some of these methods, which methods are herein incorporated by reference in their entirety, can be found, for example, in PCT Publication Nos. WO 98/44151, WO 00/18957, and WO 2006/08413; and U.S. Pat. Nos. 6,143,496, 6,833,246, and 7,754,429; and U.S. Patent Application Publication Nos. U.S. 2010/0227329 and U.S. 2009/0099041.

Various embodiments of the present disclosure are described for purposes of illustration, in the context of use with vectors containing a library of nucleic acid fragments (e.g., genomic or cDNA library). However, as those skilled in the art will appreciate upon reviewing this disclosure, use with other nucleic acid libraries or methods for making a library of nucleic acid fragments may also be suitable.

In certain embodiments, a double-stranded nucleic acid library comprises a plurality of target nucleic acid molecules and a plurality of random cyphers, wherein the nucleic acid library comprises molecules having a formula of $X^a$—Y—$X^b$ (in 5' to 3' order), wherein (a) $X^a$ comprises a first random cypher, (b) Y comprises a target nucleic acid molecule, and (c) $X^b$ comprises a second random cypher, wherein each of the plurality of random cyphers have a length of about 5 to about 50 nucleotides. In certain embodiments, the double-stranded sequence of the $X^a$ cypher for each target nucleic acid molecule is different from the double-stranded sequence of the $X^b$ cypher. In certain other embodiments, the double-stranded $X^a$ cypher is identical to the $X^b$ cypher for one or more target nucleic acid molecules, provided that the double-stranded cypher for each target nucleic acid molecule is different.

In further embodiments, the plurality or pool of random cyphers used in the double-stranded nucleic acid molecule library or vector library comprise from about 5 nucleotides to about 40 nucleotides, about 5 nucleotides to about 30 nucleotides, about 6 nucleotides to about 30 nucleotides, about 6 nucleotides to about 20 nucleotides, about 6 nucleotides to about 10 nucleotides, about 6 nucleotides to about 8 nucleotides, about 7 nucleotides to about 9 or about 10 nucleotides, or about 6, about 7 or about 8 nucleotides. In certain embodiments, a cypher preferably has a length of about 6, about 7, about 8, about 9, about 10, about 11, about 12, about 13, about 14, about 15, about 16, about 17, about 18, about 19, or about 20 nucleotides. In certain embodiments, a pair of random cyphers associated with nucleic acid sequences or vectors will have different lengths or have the same length. For example, a target nucleic acid molecule or vector may have an upstream (5') first random cypher of about 6 nucleotides in length and a downstream (3') second random cypher of about 9 nucleotides in length, or a target nucleic acid molecule or vector may have an upstream (5') first random cypher of about 7 nucleotides in length and a downstream (3') second random cypher of about 7 nucleotides in length.

In certain embodiments, both the $X^a$ cypher and the $X^b$ cypher each comprise 6 nucleotides, 7 nucleotides, 8 nucleotides, 9 nucleotides, 10 nucleotides, 11 nucleotides, 12 nucleotides, 13 nucleotides, 14 nucleotides, 15 nucleotides, 16 nucleotides, 17 nucleotides, 18 nucleotides, 19 nucleotides, or 20 nucleotides. In certain other embodiments, the $X^a$ cypher comprises 6 nucleotides and the $X^b$ cypher comprises 7 nucleotides or 8 nucleotides; or the $X^a$ cypher comprises 7 nucleotides and the $X^b$ cypher comprises 6 nucleotides or 8 nucleotides; or the $X^a$ cypher comprises 8 nucleotides and the $X^b$ cypher comprises 6 nucleotides or 7 nucleotides; or the $X^a$ cypher comprises 10 nucleotides and the $X^b$ cypher comprises 11 nucleotides or 12 nucleotides.

The number of nucleotides contained in each of the random cyphers or barcodes will govern the total number of possible barcodes available for use in a library. Shorter barcodes allow for a smaller number of unique cyphers, which may be useful when performing a deep sequence of one or a few nucleotide sequences, whereas longer barcodes may be desirable when examining a population of nucleic acid molecules, such as cDNAs or genomic fragments. In certain embodiments, multiplex sequencing may be desired when targeting specific nucleic acid molecules, specific genomic regions, smaller genomes, or a subset of cDNA transcripts. Multiplex sequencing involves amplifying two or more samples that have been pooled into, for example, a single lane of a flow cell for bridge amplification to exponentially increase the number of molecules analyzed in a single run without sacrificing time or cost. In related embodiments, a unique index sequence (comprising a length ranging from about 4 nucleotides to about 25 nucleotides) specific for a particular sample is included with each dual cypher vector library. For example, if ten different samples are being pooled in preparation for multiplex sequencing, then ten different index sequences will be used such that ten dual cypher vector libraries are used in which each library has a single, unique index sequence identifier (but each library has a plurality of random cyphers).

For example, a barcode of 7 nucleotides would have a formula of 5'-NNNNNNN-3' (SEQ ID NO.:1), wherein N may be any naturally occurring nucleotide. The four naturally occurring nucleotides are A, T, C, and G, so the total number of possible random cyphers is $4^7$, or 16,384 possible random arrangements (i.e., 16,384 different or unique cyphers). For 6 and 8 nucleotide barcodes, the number of random cyphers would be 4,096 and 65,536, respectively. In certain embodiments of 6, 7 or 8 random nucleotide cyphers, there may be fewer than the pool of 4,094, 16,384 or 65,536 unique cyphers, respectively, available for use when excluding, for example, sequences in which all the nucleotides are identical (e.g., all A or all T or all C or all G) or when excluding sequences in which three contiguous nucleotides are identical or when excluding both of these types of molecules. In addition, the first about 5 nucleotides to about 20 nucleotides of the target nucleic acid molecule sequence may be used as a further identifier tag together with the sequence of an associated random cypher.

In still further embodiments, a double-stranded nucleic acid library comprises a plurality of target nucleic acid molecules and a plurality of random cyphers, wherein the nucleic acid library comprises molecules having a formula of $X^a$—Y—$X^b$ (in 5' to 3' order), wherein (a) $X^a$ comprises a first random cypher, (b) Y comprises a target nucleic acid molecule, and (c) $X^b$ comprises a second random cypher, wherein each of the plurality of random cyphers have a length of about 5 to about 50 nucleotides and wherein (i) at least two of those nucleotides are different in each cypher or (ii) each cypher does not contain three contiguous nucleotides that are identical. In certain embodiments wherein each cypher does not contain three contiguous nucleotides that are identical, the double-stranded $X^a$ cypher is identical to the $X^b$ cypher for one or more target nucleic acid molecules, provided that the double-stranded cypher for each target nucleic acid molecule is different.

In yet further embodiments, a double-stranded nucleic acid library comprises a plurality of target nucleic acid molecules and a plurality of random cyphers, wherein the nucleic acid library comprises molecules having a formula of $X^a$—$X^b$—Y, $X^b$—$X^a$—Y, $X^a$—$X^b$, Y—$X^a$, $X^a$—Y, $X^a$—Y, Y—$X^a$, or Y—$X^b$ (in 5' to 3' order), wherein (a) $X^a$ comprises a first random cypher, (b) Y comprises a target nucleic acid molecule, and (c) $X^b$ comprises a second random cypher; wherein each of the plurality of random cyphers have a length of about 5 to about 50 nucleotides.

In any of the embodiments described herein, an $X^a$ cypher further comprises about a 5 nucleotide to about a 20 nucleotide sequence of the target nucleic acid molecule that is downstream of the $X^a$ cypher, or an $X^b$ cypher further comprises about a 5 nucleotide to about a 20 nucleotide sequence of the target nucleic acid molecule that is upstream of the $X^b$ cypher, or an $X^a$ cypher and $X^b$ cypher further comprise about a 5 nucleotide to about a 20 nucleotide sequence of the target nucleic acid molecule that is downstream or upstream, respectively, of each cypher.

In yet further embodiments, a first target molecule is associated with and disposed between a first random cypher $X^a$ and a second random cypher $X^b$, a second target molecule is associated with and disposed between a third random cypher $X^a$ and a fourth random cypher $X^b$, and so on, wherein the target molecules of a library or of a vector library each has a unique $X^a$ cypher (i.e., none of the $X^a$ cyphers have the same sequence) and each has a unique $X^b$ cypher (i.e., none of the $X^b$ cyphers have the same sequence), and wherein none or only a minority of the $X^a$ and $X^b$ cyphers have the same sequence.

For example, if the length of the random cypher is 7 nucleotides, then there will a total of 16,384 different barcodes available as first random cypher X, and second random cypher $X^b$. In this case, if a first target nucleic acid molecule is associated with and disposed between random cypher $X^a$ number 1 and random cypher $X^b$ number 2 and a second target nucleic acid molecule is associated with and disposed between random cypher $X^a$ number 16,383 and random cypher $X^b$ number 16,384, then a third target nucleic acid molecule can only be associated with and disposed between any pair of random cypher numbers selected from numbers 3 to 16,382, and so on for each target nucleic acid molecule of a library until each of the different random cyphers have been used (which may or may not be all 16,382). In this embodiment, each target nucleic acid molecule of a library will have a unique pair of cyphers that differ from each of the other pairs of cyphers found associated with each other target nucleic acid molecule of the library.

In any of the embodiments described herein, random cypher sequences from a particular pool of cyphers (e.g., pools of 4,094, 16,384 or 65,536 unique cyphers) may be used more than once. In further embodiments, each target nucleic acid molecule or a subset of target molecules has a different (unique) pair of cyphers. For example, if a first target molecule is associated with and disposed between random cypher number 1 and random cypher number 100, then a second target molecule will need to be flanked by a different dual pair of cyphers—such as random cypher number 1 and random cypher number 65, or random cypher number 486 and random cypher number 100—which may be any combination other than 1 and 100. In certain other embodiments, each target nucleic acid molecule or a subset of target molecules has identical cyphers on each end of one or more target nucleic acid molecules, provided that the double-stranded cypher for each target nucleic acid molecule is different. For example, if a first target molecule is flanked by cypher number 10, then a second target molecule having identical cyphers on each end will have to have a different cypher—such as random cypher number 555 or the like—which may be any other cypher other than 10. In still further embodiments, target nucleic acid molecules of the nucleic acid molecule library will each have dual unique cyphers $X^a$ and $X^b$, wherein none of the $X^a$ cyphers have the same sequence as any other $X^a$ cypher, none of the $X^b$ cyphers have the same sequence as any other $X^b$ cypher, and none of the $X^a$ cyphers have the same sequence as any $X^b$ cypher. In still further embodiments, target nucleic acid molecules of the nucleic acid molecule library will each have a unique pair of $X^a$—$X^b$ cyphers wherein none of the $X^a$ or $X^b$ cyphers have the same sequence. A mixture of any of the aforementioned embodiments may make up a nucleic acid molecule library of this disclosure.

In any of the embodiments described herein, the plurality of target nucleic acid molecules that together are used to generate a nucleic acid molecule library (or used for insertion into a vector to generate a vector library containing a plurality of target nucleic acid molecules) may each have a length that ranges from about 10 nucleotides to about 10,000 nucleotides, from about 50 nucleotides to about 5,000 nucleotides, from about 100 nucleotides to about 1,000 nucleotides, or from about 150 nucleotides to about 750 nucleotides, or from about 250 nucleotides to about 500 nucleotides.

In any of the embodiments described herein, the plurality of random cyphers may further be linked to a first nucleic acid molecule priming site (PS1), linked to a second nucleic acid molecule priming site (PS2), or linked to both a first and a second nucleic acid molecule priming site. In certain embodiments, a plurality of random cyphers may each be associated with and disposed between a first nucleic acid molecule priming site (PS1) and a second nucleic acid molecule priming site (PS2), wherein the double-stranded sequence of PS1 is different from the double-stranded sequence of PS2. In certain embodiments, each pair of $X^a$—$X^b$ cyphers may be associated with and disposed between an upstream and a downstream nucleic acid molecule priming site (PS1) (see, e.g., FIG. 2).

In any of the embodiments described herein, a first nucleic acid molecule priming site PS1 will be located upstream (5') of the first random cypher $X^a$ and the first nucleic acid molecule priming site PS1 will also be located downstream (3') of the second random cypher $X^b$. In certain embodiments, an oligonucleotide primer complementary to the sense strand of PS1 can be used to prime a sequencing reaction to obtain the sequence of the sense strand of the first random cypher $X^a$ or to prime a sequencing reaction to obtain the sequence of the anti-sense strand of the second random cypher $X^b$, whereas an oligonucleotide primer complementary to the anti-sense strand of PS1 can be used to prime a sequencing reaction to obtain the sequence of the anti-sense strand of the first random cypher $X^a$ or to prime a sequencing reaction to obtain the sequence of the sense strand of the second random cypher $X^b$.

In any of the embodiments described herein, the second nucleic acid molecule priming site PS2 will be located downstream (3') of the first random cypher $X^a$ and the second nucleic acid molecule priming site PS2 will also be located upstream (5') of the second random cypher $X^b$. In certain embodiments, an oligonucleotide primer complementary to the sense strand of PS2 can be used to prime a sequencing reaction to obtain the sequence of the sense strand from the 5'-end of the associated double-stranded target nucleic acid molecule or to prime a sequencing reaction to obtain the sequence of the anti-sense strand from the 3'-end of the associated double-stranded target nucleic acid molecule, whereas an oligonucleotide primer complementary to the anti-sense strand of PS2 can be used to prime a sequencing reaction to obtain the sequence of the anti-sense strand from the 5'-end of the associated double-stranded target nucleic acid molecule or to prime a sequencing reaction to obtain the sequence of the sense strand from the 3'-end of the associated double-stranded target nucleic acid molecule.

Depending on the length of the target nucleic acid molecule, the entire target nucleic acid molecule sequence may be obtained if it is short enough or only a portion of the entire target nucleic acid molecule sequence may be obtained if it is longer than about 100 nucleotides to about 250 nucleotides. An advantage of the compositions and methods of the instant disclosure is that even though a target nucleic acid molecule is too long to obtain sequence data for the entire molecule or fragment, the sequence data obtained from one end of a double-stranded target molecule can be specifically linked to sequence data obtained from the opposite end or from the second strand of that same double-stranded target molecule because each target molecule in a library of this disclosure will have double-stranded cyphers, or a unique $X^a$—$X^b$ pair of cyphers. Linking the sequence data of the two strands allows for sensitive identification of "true" mutations wherein deeper sequencing actually increases the sensitivity of the detection, and these methods can provide sufficient data to quantify the number of artifact mutations.

In any of the embodiments described herein, a plurality of random cyphers may further comprise a first restriction endonuclease recognition sequence (RE1) and a second restriction endonuclease recognition sequence (RE2), wherein the first restriction endonuclease recognition sequence RE is located upstream (5') of the first random cypher $X^a$ and the second restriction endonuclease recognition sequence RE2 is located downstream (3') of the second random cypher $X^b$. In certain embodiments, a first restriction endonuclease recognition sequence RE1 and a second restriction endonuclease recognition sequence RE2 are the same or different. In certain embodiments, RE1, RE2, or both RE1 and RE2 are "rare-cutter" restriction endonucleases that have a recognition sequence that occurs only rarely within a genome or within a target nucleic acid molecule sequence or are "blunt-cutters" that generate nucleic acid molecules with blunt ends after digestion (e.g., SmaI). Such rare cutter enzymes generally have longer recognition sites with seven- or eight-nucleotide or longer recognition sequences, such as AarI, AbeI, AscI, AsSI, BbvCI, BstRZ246I, BstSWI, CciNI, CsiBI, CspBI, FseI, NotI, MchAI, MspSWI, MssI, PacI, PmeI, SbfI, SdaI, SgfI, SmiI, SrfI, Sse232I, Sse8387I, SwaI, TaqII, VpaK32I, or the like.

In certain embodiments, a nucleic acid molecule library comprises nucleic acid molecules having a formula of 5'-RE1-PS1-$X^a$—PS2-Y—PS2-$X^b$—PS1-RE2-3', wherein RE1 is a first restriction endonuclease recognition sequence, PS1 is a first nucleic acid molecule priming site, PS2 is a second nucleic acid molecule priming site, RE2 is a second restriction endonuclease recognition sequence, Y comprises a target nucleic acid molecule, and $X^a$ and $X^b$ are cyphers comprising a length ranging from about 5 nucleotides to about 50 nucleotides or about 6 nucleotides to about 15 nucleotides or about 7 nucleotides to about 9 nucleotides. In further embodiments, RE1 and RE2 are sequences recognized by the same restriction endonuclease or an isoschizomer or neoschizomer thereof, or RE1 and RE2 have different sequences recognized by different restriction endonucleases. In further embodiments, PS1 and PS2 have different sequences. In further embodiments, target nucleic acid molecules of the nucleic acid molecule library will each have dual unique cyphers $X^a$ and $X^b$, wherein none of the $X^a$ cyphers have the same sequence as any other $X^a$ cypher, none of the $X^b$ cyphers have the same sequence as any other $X^b$ cypher, and none of the $X^a$ cyphers have the same sequence as any $X^b$ cypher. In still further embodiments, target nucleic acid molecules of the nucleic acid molecule library will each have a unique cypher or pair of $X^a$—$X^b$ cyphers wherein none of the $X^a$ or $X^b$ cyphers have the same sequence.

Also contemplated in the present disclosure is using a library of double-stranded barcoded or dual double-stranded barcoded target nucleic acid molecules for amplification and sequencing reactions to detect true mutations. In order to facilitate certain amplification or sequencing methods, other features may be included in the compositions of the instant disclosure. For example, bridge amplification may involve ligating adapter sequences to each end of a population of target nucleic acid molecules. Single-stranded oligonucleotide primers complementary to the adapters are immobilized on a solid substrate, the target molecules containing the adapter sequences are denatured into single strands, and hybridized to complementary primers on the solid substrate. An extension reaction is used to copy the hybridized target molecule and the double-stranded product is denatured into single strands again. The copied single strands then loop over (form a "bridge") and hybridize with a complementary primer on the solid substrate, upon which the extension reaction is run again. In this way, many target molecules may be amplified at the same time and the resulting product is subject to massive parallel sequencing.

In certain embodiments, a nucleic acid molecule library comprises nucleic acid molecules having a formula of 5'-RE1-AS-PS1-$X^a$—PS2-Y—PS2-$X^b$—PS1-AS-RE2-3', wherein RE1 and RE2 are first and second restriction endonuclease recognition sequences, PS1 and PS2 are a first and second nucleic acid molecule priming sites, AS is an adapter sequence comprising a length ranging from about 20 nucleotides to about 100 nucleotides, Y comprises a target nucleic acid molecule, and $X^a$ and $X^b$ are cyphers comprising a length ranging from about 5 nucleotides to about 50 nucleotides or about 6 nucleotides to about 15 nucleotides or about 7 nucleotides to about 9 nucleotides.

In further embodiments, a nucleic acid molecule library comprises nucleic acid molecules having a formula of 5'-RE-AS-PS1-$X^a$—Y—$X^b$—PS1-AS-RE2-3', wherein RE1 and RE2 are first and second restriction endonuclease recognition sequences, PS1 is a first nucleic acid molecule priming site, AS is an adapter sequence comprising a length ranging from about 20 nucleotides to about 100 nucleotides, Y comprises a target nucleic acid molecule, and $X^a$ and $X^b$ are cyphers comprising a length ranging from about 5 nucleotides to about 50 nucleotides or about 6 nucleotides to about 15 nucleotides or about 7 nucleotides to about 9 nucleotides. In related embodiments, the AS adapter sequence of the aforementioned vector may further comprise a PS2 that is a second nucleic acid priming site or the PS2 may be a part of the original AS sequence. In still further embodiments, the nucleic acid molecule library may further comprise an index sequence (comprising a length ranging from about 4 nucleotides to about 25 nucleotides) located between each of the first and second AS and the PS1 so that the library can be pooled with other libraries having different index sequences to facilitate multiplex sequencing (also referred to as multiplexing) either before or after amplification.

Each of the aforementioned dual barcoded target nucleic acid molecules may be assembled into a carrier library in the form of, for example, a self-replicating vector, such as a plasmid, cosmid, YAC, viral vector or other vectors known in the art. In certain embodiments, any of the aforementioned double-stranded nucleic acid molecules comprising a plurality of target nucleic acid molecules and a plurality of random cyphers, are contained in a vector. In still further embodiments, such a vector library is carried in a host cell, such as bacteria, yeast, or mammalian cells.

Figure 2:
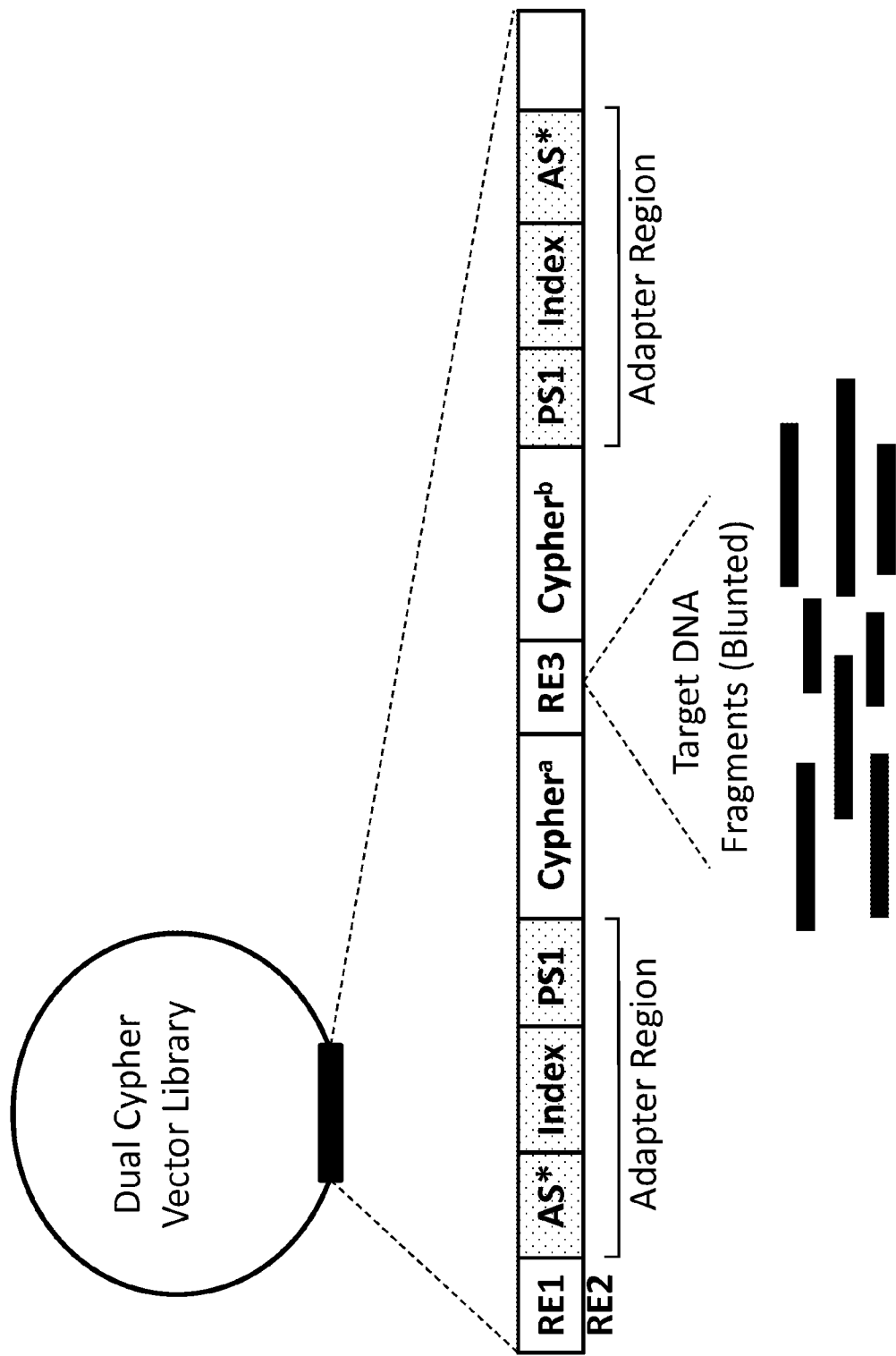
FIG. 2 is a cartoon illustration of an exemplary vector of the present disclosure, wherein adaptor sequences are included and are useful for, for example, bridge amplification methods before sequencing.

The present disclosure also provides vectors useful for generating a library of dual barcoded target nucleic acid molecules according to this disclosure. Exemplary vectors comprising cyphers and other elements of this disclosure are illustrated in FIGS. 1 and 2.

In certain embodiments, there are provided a plurality of nucleic acid vectors, comprising a plurality of random cyphers, wherein each vector comprises a region having a formula of 5'-RE1-PS1-$X^a$—PS2-RE3-PS2-$X^b$—PS1-RE2-3', wherein (a) RE1 is a first restriction endonuclease recognition sequence, (b) PS1 is a first nucleic acid molecule priming site, (c) $X^a$ comprises a first random cypher, (d) RE3 is a third restriction endonuclease recognition sequence, wherein RE3 is a site into which a target nucleic acid molecule can be inserted, (c) $X^b$ comprises a second random cypher, (f) PS2 is a second nucleic acid molecule priming site, and (g) RE2 is a second restriction endonuclease recognition sequence; and wherein each of the plurality of random cyphers comprise a length ranging from about 5 nucleotides to about 50 nucleotides, preferably from about 7 nucleotides to about 9 nucleotides; and wherein the plurality of nucleic acid vectors are useful for preparing a double-stranded nucleic acid molecule library in which each vector has a different target nucleic acid molecule insert. In certain embodiments, the sequence of the $X^a$ cypher is different from the sequence of the $X^b$ cypher in each vector (that is, each vector has a unique pair). In further embodiments, the plurality of nucleic acid vectors may further comprise at least one adapter sequence (AS) between RE1 and PS1 and at least one AS between PS1 and RE2, or comprise at least one AS between RE1 and $X^a$ cypher and at least one AS between $X^b$ cypher and RE2, wherein the AS optionally has a priming site.

In further vector embodiments, the plurality of random cyphers can each have the same or different number of nucleotides, and comprise from about 6 nucleotides to about 8 nucleotides to about 10 nucleotides to about 12 nucleotides to about 15 nucleotides. In still other embodiments, a plurality of target nucleic acid molecules comprising from about 10 nucleotides to about 10,000 nucleotides or comprising from about 100 nucleotides to about 750 nucleotides or to about 1,000 nucleotides, may be inserted into the vector at RE3. In certain embodiments, RE3 will cleave DNA into blunt ends and the plurality of target nucleic acid molecules ligated into this site will also be blunt-ended.

In certain embodiments, the plurality of nucleic acid vectors wherein each vector comprises a region having a formula of 5'-RE-PS1-$X^a$—PS2-RE3-PS2-$X^b$—PS1-RE2-3' the $X^a$ cyphers and $X^b$ cyphers on each vector is sequenced before a target nucleic acid molecule is inserted into each vector. In further embodiments, the plurality of nucleic acid vectors wherein each vector comprises a region having a formula of 5'-RE1-PS1-$X^a$—PS2-RE3-PS2-$X^b$—PS1-RE2-3' the $X^a$ cyphers and $X^b$ cyphers on each vector is sequenced after a target nucleic acid molecule is inserted into each vector or is sequenced at the same time a target nucleic acid molecule insert is sequenced.

The dual barcoded target nucleic acid molecules and the vectors containing such molecules of this disclosure may further be used in sequencing reactions to determine the sequence and mutation frequency of the molecules in the library. In certain embodiments, this disclosure provides a method for obtaining a nucleic acid sequence by preparing a double-stranded dual barcoded nucleic acid library as described herein and then sequencing each strand of the plurality of target nucleic acid molecules and plurality of random cyphers. In certain embodiments, target nucleic acid molecules and and associated cyphers are excised for sequencing directly from the vector using restriction endonuclease enzymes prior to amplification. In certain embodiments, next generation sequencing methods are used to determine the sequence of library molecules, such as sequencing by synthesis, pyrosequencing, reversible dye-terminator sequencing or polony sequencing.

In still further embodiments, there are provided methods for determining the error rate due to amplification and sequencing by determining the sequence of one strand of a target nucleic acid molecule associated with the first random cypher and aligning with the sequence of the complementary strand associated with the second random cypher to distinguish between a pre-existing mutation and an amplification or sequencing artifact mutation, wherein the measured sequencing error rate will range from about $10^{-6}$ to about $5 \times 10^{-6}$ to about $10^{-7}$ to about $5 \times 10^{-7}$ to about $10^{-8}$ to about $10^{-9}$. In other words, using the methods of this disclosure, a person of ordinary skill in the art can associate each DNA sequence read to an original template DNA. Given that both strands of the original double-stranded DNA are barcoded with associated barcodes, this increases the sensitivity of the sequencing base call by more easily identifying artifact "mutations" sequence changes introduced during the sequencing process.

In certain embodiments, the compositions and methods of this instant disclosure will be useful in detecting rare mutants against a large background signal, such as when monitoring circulating tumor cells; detecting circulating mutant DNA in blood, monitoring or detecting disease and rare mutations by direct sequencing, monitoring or detecting disease or drug response associated mutations. Additional embodiments may be used to quantify DNA damage, quantify or detect mutations in viral genomes (e.g., HIV and other viral infections) or other infectious agents that may be indicative of response to therapy or may be useful in monitoring disease progression or recurrence. In yet other embodiments, these compositions and methods may be useful in detecting damage to DNA from chemotherapy, or in detection and quantitation of specific methylation of DNA sequences.

EXAMPLES

Example 1

Dual Cypher Sequencing of a Tumor Genomic Library

Cancer cells contain numerous clonal mutations, i.e., mutations that are present in most or all malignant cells of a tumor and have presumably been selected because they confer a proliferative advantage. An important question is whether cancer cells also contain a large number of random mutations, i.e., randomly distributed unselected mutations that occur in only one or a few cells of a tumor. Such random mutations could contribute to the morphologic and functional heterogeneity of cancers and include mutations that confer resistance to therapy. The instant disclosure provides compositions and methods for distinguishing clonal mutations from random mutations.

To examine whether malignant cells exhibit a mutator phenotype resulting in the generation of random mutations throughout the genome, dual cypher sequencing of present disclosure will be performed on normal and tumor genomic libraries. Briefly, genomic DNA from patient-matched normal and tumor tissue is prepared using Qiagen® kits (Valencia, Calif.), and quantified by optical absorbance and quantitative PCR (qPCR). The isolated genomic DNA is fragmented to a size of about 150-250 base pairs (short insert library) or to a size of about 300-700 base pairs (long insert library) by shearing. The DNA fragments having overhang ends are repaired (i.e., blunted) using T4 DNA polymerase (having both 3' to 5' exonuclease activity and 5' to 3' polymerase activity) and the 5'-ends of the blunted DNA are phosphorylated with T4 polynucleotide kinase (Quick Blunting Kit I, New England Biolabs), and then purified. The end-repaired DNA fragments are ligated into the SmaI site of the library of dual cypher vectors shown in FIG. 2 to generate a target genomic library.

The ligated cypher vector library is purified and the target genomic library fragments are amplified by using, for example, the following PCR protocol: 30 seconds at 98° C.; five to thirty cycles of 10 seconds at 98° C., 30 seconds at 65° C., 30 seconds at 72° C.; 5 minutes at 72° C.; and then store at 4° C. The amplification is performed using sense strand and anti-sense strand primers that anneal to a sequence located within the adapter region (in certain embodiments, the primer will anneal to a sequence upstream of the AS), and is upstream of the unique cypher and the target genomic insert (and, if present, upstream of an index sequence if multiplex sequencing is desired; see, e.g., FIG. 2) for Illumina bridge sequencing. The sequencing of the library described above will be performed using, for example, an Illumina® Genome Analyzer II sequencing instrument as specified by the manufacturer.

The unique cypher tags are used to computationally deconvolute the sequencing data and map all sequence reads to single molecules (i.e., distinguish PCR and sequencing errors from real mutations). Base calling and sequence alignment will be performed using, for example, the Eland pipeline (Illumina, San Diego, Calif.). The data generated will allow identification of tumor heterogeneity at the single-nucleotide level and reveal tumors having a mutator phenotype.

Example 2

Dual Cypher Sequencing of a mtDNA Library

Mutations in mitochondrial DNA (mtDNA) lead to a diverse collection of diseases that are challenging to diagnose and treat. Each human cell has hundreds to thousands of mitochondrial genomes and disease-associated mtDNA mutations are homoplasmic in nature, i.e., the identical mutation is present in a preponderance of mitochondria within a tissue (Taylor and Turnbull, Nat. Rev. Genet. 6:389, 2005; Chatterjee et al., Oncogene 25:4663, 2006). Although the precise mechanisms of mtDNA mutation accumulation in disease pathogenesis remain elusive, multiple homoplasmic mutations have been documented in colorectal, breast, cervical, ovarian, prostate, liver, and lung cancers (Copeland et al., Cancer Invest. 20:557, 2002; Brandon et al., Oncogene 25:4647, 2006). Hence, the mitochondrial genome provides excellent potential as a specific biomarker of disease, which may allow for improved treatment outcomes and increased overall survival.

Dual cypher sequencing of present disclosure can be leveraged to quantify circulating tumor cells (CTCs) and circulating tumor mtDNA (ctmtDNA) could be used to diagnose and stage cancer, assess response to therapy, and evaluate progression and recurrence after surgery. First, mtDNA isolated for prostatic cancer and peripheral blood cells from the same patient will be sequenced to identify somatic homoplasmic mtDNA mutations. These mtDNA biomarkers will be statistically assessed for their potential fundamental and clinical significance with respect to Gleason score, clinical stage, recurrence, therapeutic response, and progression.

Once specific homoplasmic mutations from individual tumors are identified, patient-matched blood specimens will be examined for the presence of identical mutations in the plasma and buffy coat to determine the frequencies of ctmtDNA and CTCs, respectfully. This will be accomplished by using the dual cypher sequencing technology of this disclosure, and as described in Example 1, to sensitively monitor multiple mtDNA mutations concurrently. The distribution of CTCs in peripheral blood from patients with varying PSA serum levels and Gleason scores will be determined.

Example 3

High-Resolution Detection of TP53 Mutations

A recent genomics study determined that TP53 is mutated in 96% of high grade serous ovarian carcinoma (HGSC), responsible for two-thirds of all ovarian cancer deaths (Cancer Genome Atlas Research Network, Nature 474:609, 2011), and current models indicate that TP53 loss is an early event in HGSC pathogenesis (Bowtell, Nat. Rev. Cancer 10:803, 2010). Thus, the near universality and early occurrence of TP53 mutations in HGSC make TP53 a promising biomarker candidate for early detection and disease monitoring of HGSC. Dual cypher sequencing of present disclosure was used to detect somatic TP53 mutations that arose during replication in E. coli.

Dual Cypher Vector Construction

An oligonucleotide containing EcoRI and BamHI restriction enzyme sites, adapter sequences, indices, and random 7-nucleotide barcodes flanking a SmaI restriction enzyme site with the following sequence was made (Integrated DNA Technologies):

(SEQ ID NO.: 2)
GATACAGGATCCAATGATACGGCGACCACCGAGATCTACACTAGATCGC

GCCTCCCTCGCGCCATCAGAGATGTGTATAAGAGACAGNNNNNNNCCCG

GGNNNNNNNCTGTCTCTTATACACATCTCTGAGCGGGCTGGCAAGGCAG

ACCGTAAGGCGAATCTCGTATGCCGTCTTCTGCTTGGAATTCGATACA.

To amplify and create a double-stranded product from this single-stranded DNA oligonucleotide, 30 cycles of PCR were performed using PfuUltra High-Fidelity DNA Polymerase (Agilent Technologies) as per the manufacturer's instructions (forward primer sequence: GATACAGGATC-CAATGATACGG, SEQ ID NO.:3; reverse primer sequence: TGTATCGAATTCCAAGCAGAAG, SEQ ID NO.:4). The following cycling conditions were used: 95° C. for 2 minutes, followed by 30 cycles of 95° C. for 1 minute and 64° C. for 1 minute. The double-stranded nature of the product was verified using a SmaI (New England BioLabs) restriction digest. The product was then purified (Zymo Research DNA Clean & Concentrator-5) and subjected to EcoRI/BamHI restriction digest using BamHI-HF (New England BioLabs) and EcoRI-HF (New England BioLabs) to prepare the construct for ligation into an EcoRI/BamHI-digested pUC19 backbone. Digested vector and construct were run on a 1.5% UltraPure Low-Melting Point Agarose (Invitrogen) electrophoresis gel with 1× SybrSafe (Invitrogen) and the appropriate bands were excised. The DNA in the gel fragments was purified using a Zymo-Clean gel DNA recovery kit (Zymo Research) and quantified using a spectrophotometer (Nanophotometer, Implen). Ligation reactions using T4 DNA ligase HC (Invitrogen) and a 1:3 vector to insert molar ratio at room temperature for 2 hours were carried out, then ethanol precipitated, and resuspended in water. Purified DNA (2 µl) was electroporated into ElectroMAX DH10B T1 Phage Resistant Cells (Invitrogen). The transformed cells were plated at a 1:100 dilution on LB agar media containing 100 µg/mL carbenicillin and incubated overnight at 37° C. to determine colony counts, and the remainder of the transformation was spiked into LB cultures for overnight growth at 37° C. The DNA from the overnight cultures was purified using the QIAquick Spin Miniprep Kit (Qiagen).

Figure 3A:
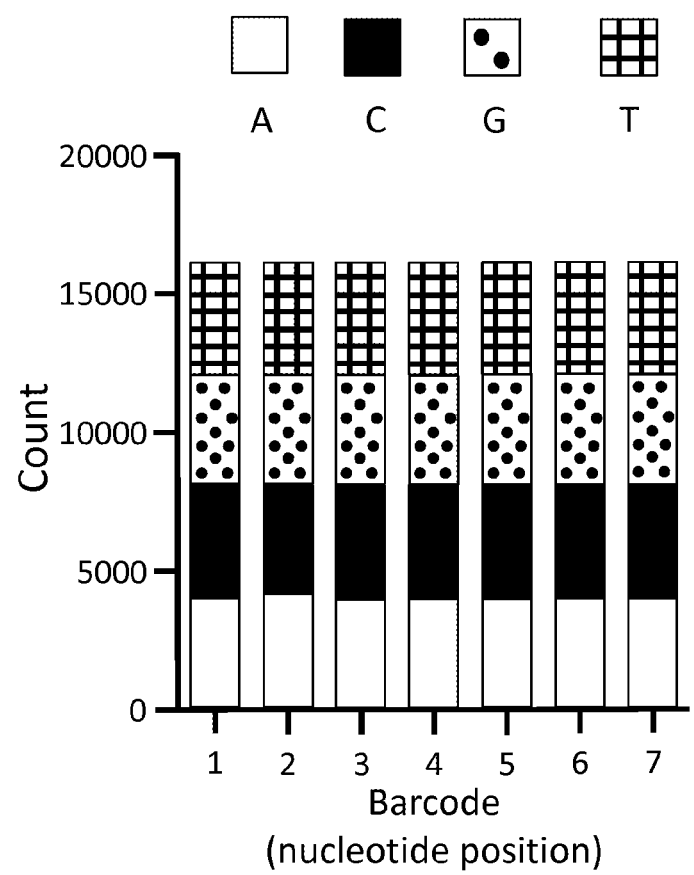
FIGS. 3A and 3B show characteristics of a cypher library and the detection of true mutations. (A) Data generated in a single next generation sequence run on MiSeq® demonstrates broad coverage and diversity at the upstream seven base pair cypher in a vector library, wherein the vector used is illustrated in FIG. 2. (B) Cypher Seq eliminates errors introduced during library preparation and sequencing. Target nucleic acid molecules were ligated into a cypher vector library containing previously catalogued dual, double-stranded cyphers. The target sequences were amplified and sequenced. All sequencing reads having identical cypher pairs, along with their reverse complements, were grouped into families. Comparison of family sequences allowed for generation of a consensus sequence wherein 'mutations' (errors) arising during library preparation (open circle) and during sequencing (gray circle and triangle) were computationally eliminated. Generally, mutations that are present in all or substantially all reads (black diamond) from the same cypher and its reverse complement are counted as true mutations.

A single next generation sequencing run on MiSeq® demonstrated optimal coverage and diversity at the upstream seven basepair cypher in the vector library. FIG. 3A shows that the each nucleotide was detected at approximately the same rate at each random position of the cypher (here the 5' cyphers were sequenced).

TP53 Exon 4 Library Construction

Briefly, SKOV-3 (human ovarian carcinoma cell line) cells were grown in McCoy's 5a Medium supplemented with 10% Fetal Bovine Serum, 1.5 mM/L-glutamine, 2200 mg/L sodium bicarbonate, and Penicillin/Streptomycin. SKOV-3 cells were harvested and DNA was extracted using a DNeasy Blood and Tissue Kit (Qiagen). PCR primers were designed to amplify exon 4 of human TP53; forward primer sequence: TCTGTCTCCTTCCTCTTCCTACA (SEQ ID NO.:5) and reverse primer sequence: AACCAGCCCTGTCGTCTCT (SEQ ID NO.:6). Thirty cycles of PCR were performed on SKOV-3 DNA using 0.5 µM primers and GoTaq Hot Start Colorless Master Mix (Promega) under the following cycling conditions: 95° C. for 2 minutes; 30 cycles of 95° C. for 30 seconds, 63° C. for 30 seconds, 72° C. for 1 minute; followed by 72° C. for 5 minutes. Each PCR product was then cloned into TOPO vectors (Invitrogen), transformed into One Shot TOP10 Chemically Competent *E. coli* cells (Invitrogen), plated on LB agar media containing 100 µg/mL carbenicillin and incubated overnight at 37° C.

Ten colonies were picked and cultured overnight. The DNA from the overnight LB cultures was purified using the QIAquick Spin Miniprep Kit (Qiagen). Sequencing of the TOPO clones was performed using capillary electrophoresis-based sequencing on an Applied Biosystems 3730×1 DNA Analyzer. One TOPO clone containing the appropriate wild type TP53 exon 4 sequence was selected. The DNA was subjected to EcoRI digestion to excise the TP53 exon 4 insert and run on a 1.5% UltraPure Low-Melting Point Agarose gel. The TP53 exon 4 DNA band was then manually excised and purified using the Zymo-Clean gel DNA recovery kit followed by phenol/chloroform/isoamyl alcohol extraction and ethanol precipitation. The digested DNA was then blunted and phosphorylated using the Quick Blunting Kit (New England BioLabs) and purified with a phenol/chloroform/isoamyl alcohol extraction and ethanol precipitation.

The Cypher Seq vector library was digested with SmaI, treated with Antarctic Phosphatase (New England BioLabs), and run on a 1.5% UltraPure Low-Melting Point Agarose gel. The appropriate band was excised and purified using the Zymo-Clean gel DNA recovery kit, followed by phenol/chloroform/isoamyl alcohol extraction and ethanol precipitation. Blunt-end ligations of the vector and TP53 exon 4 DNA were then carried out in 20 µl reactions using T4 DNA Ligase HC (Invitrogen) and a 1:10 vector to insert molar ratio. The ligations were incubated at 16° C. overnight, ethanol precipitated, and transformed into ElectroMAX DH10b T1-phage resistant cells. Bacteria were grown overnight at 37° C. in LB containing 100 µg/mL carbenicillin and DNA was purified using the QIAquick Spin Miniprep Kit. The presence of the appropriate insert was verified by diagnostic restriction digest and gel electrophoresis.

The sequencing construct containing the Illumina adapters, barcodes, and TP53 DNA was then amplified using 10 cycles of PCR and primers designed against the adapter ends (forward primer: AATGATACGGCGACCACCGA, SEQ ID NO.:7; and reverse primer: CAAGCAGAAGACGGCATACGA, SEQ ID NO.:8). PCR cycling conditions were as follows: 95° C. for 2 minutes; 10 cycles of 95° C. for 30 seconds, 63° C. for 30 seconds, 72° C. for 1 minute; followed by 72° C. for 5 minutes. The sequencing construct was gel purified (Zymo-Clean gel DNA recovery kit), phenol/chloroform/isoamyl alcohol extracted and ethanol precipitated. The library was quantified using the Quant-iT PicoGreen assay (Invitrogen) before loading onto the Illumina MiSeq® flow cell. Finally, the library was sequenced. Sequencing was performed as instructed by the manufacturer's protocol with MiSeq® at Q30 quality level (Illumina). A Q score is defined as a property that is logarithmically related to the base calling error probabilities ($Q=-10 \log_{10}P$). In the case of an assigned Q score of 30 (Q30) to a base, this means that the probability of an incorrect base call is 1 in 1,000 times—that is, the base call accuracy (i.e., probability of a correct base call) is 99.9%-considered the gold standard for next generation sequencing. Barcodes were used to deconvolute the sequencing data.

Results

Figure 3B:
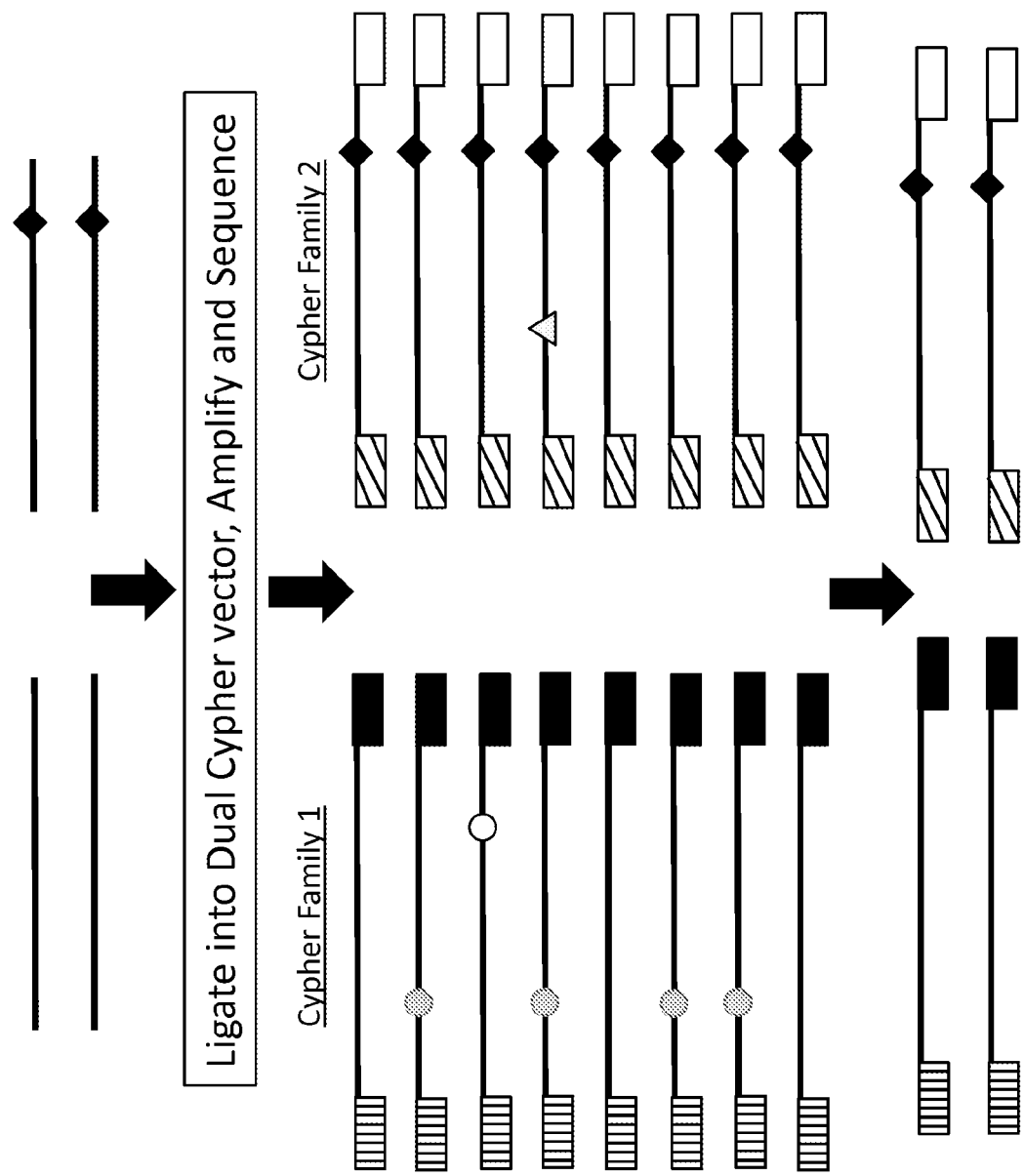

TP53 Exon 4 DNA from a dual cypher vector library produced in *E. coli* was sequenced with a depth of over a million, and all sequencing reads with identical cypher pairs and their reverse complements were grouped into families to create a consensus sequence. As illustrated in FIG. 3B, errors introduced during library preparation (open circle) and during sequencing (gray circle and triangle) were computationally eliminated from the consensus sequence and only mutations present in all reads (black diamonds, FIG. 3B) of a cypher family were counted as true mutations (see bottom of FIG. 3B).

Figure 4A:
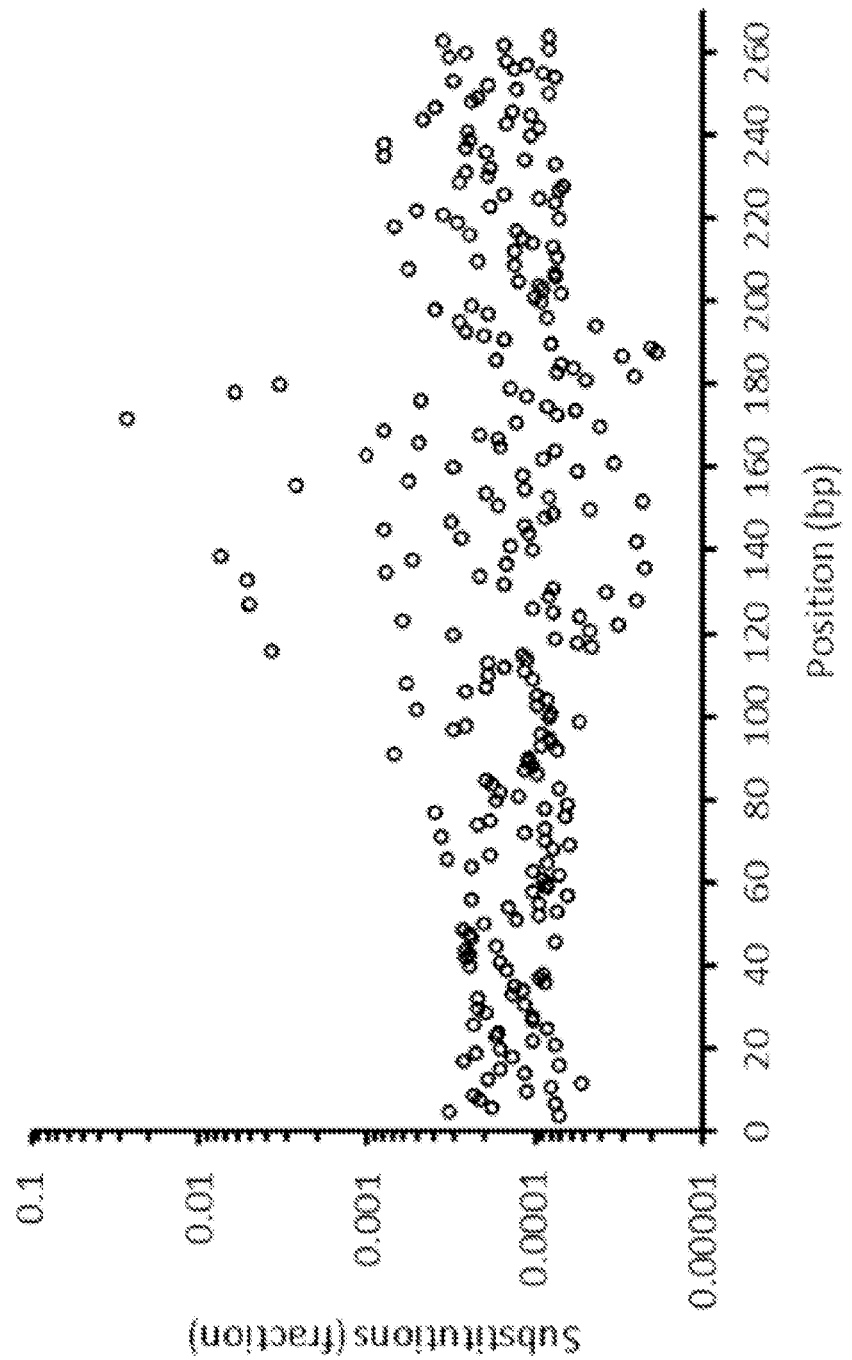
FIGS. 4A and 4B show that the cypher system can distinguish true mutations from artifact mutations. (A) Wild-type TP53 Exon 4 was ligated into a library of Cypher Seq vectors and sequenced on the Illumina MiSeq® instrument with a depth of over a million. Sequences were then compared to wild-type TP53 sequence. Detected substitutions were plotted before (A) and after correction (B) with Cypher Seq.
Figure 4B:
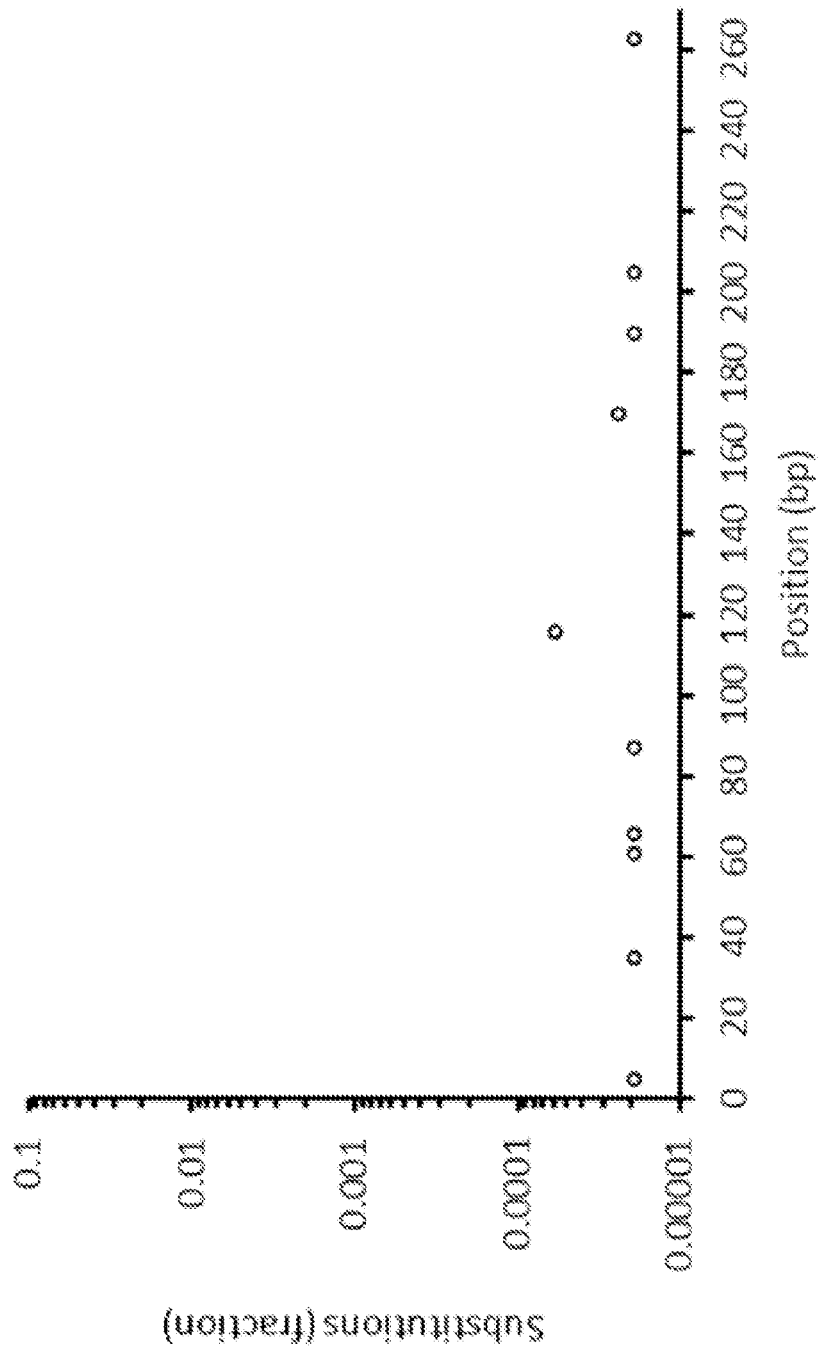

Wild-type TP53 Exon 4 sequence was compared to the actual sequence results and substitutions were plotted before (FIG. 4A) and after correction with Cypher Seq (FIG. 4B). Prior to correction, the detected error frequency was $3.9 \times 10^{-4}$/bp (FIG. 4A). In short, the initial error frequency reflects assay-related errors (e.g., PCR, sequencing, and other errors introduced after bar-coding). This means that detecting a rare mutation is difficult due to the noise-to-signal ratio being very high. After Cypher Seq correction, however, the error frequency dropped to $8.8 \times 10^{-7}$/bp (FIG. 4B). In other words, the remaining substitutions are most likely biological in nature and most likely reflect errors introduced during replication in *E. coli* prior to ligation into the barcoded vectors. Thus, true mutations (i.e., those that arise naturally in a cell during replication) are readily detectable using the cypher system of the instant disclosure.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. In general, in the following claims, the terms used should not be construed to limit the claims to specific embodiments disclosed in the specification and claims, but should be construed to include all possible embodiments along with the full scope of equivalents to which such claims are entitled. Accordingly, the claims are not limited by the disclosure.

What is claimed is:

1. A method of sequencing double-stranded cell-free DNA (cfDNA) molecules, the method comprising:
   (a) ligating double-stranded adapters to both ends of the double-stranded cfDNA molecules to form adapter-target complexes, wherein (i) the double-stranded adapters each comprise an identifier sequence, (ii) at least two adapters comprise the same identifier sequence and are ligated to different cfDNA molecules, (iii) cfDNA end sequences together with associated identifier sequences form cyphers at both ends of the cfDNA molecules; and (iv) individual adapter-target complexes comprise different pairs of cyphers;
   (b) amplifying the adapter-target complexes to produce a plurality of adapter-target amplification products from each of a first strand and a complementary second strand of the adapter-target complexes;
   (c) sequencing the adapter-target amplification products to produce a plurality of first-strand sequencing reads and a plurality of second-strand sequencing reads;
   (d) comparing the first-strand sequencing reads with the second-strand sequencing reads for each of a plurality of the adapter-target complexes; and
   (e) generating error-corrected sequences for each of a plurality of the double-stranded cfDNA molecules by distinguishing erroneous nucleotides in one strand that lack a matched base change in the complementary strand.

2. The method of claim 1, wherein the identifier sequence is a random identifier sequence.

3. The method of claim 1, wherein the identifier sequence is not completely random.

4. The method of claim 1, wherein the identifier sequence is at an end of the double-stranded adapter.

5. The method of claim 1, wherein the identifier sequence is about 5 to about 50 nucleotides in length.

6. The method of claim 5, wherein the identifier sequence is 5 to 10 nucleotides in length.

7. The method of claim 1, wherein the cfDNA end sequences comprise 5 to 20 terminal nucleotides of the double-stranded cfDNA molecules.

8. The method of claim 1, wherein the erroneous nucleotides comprise a polymerase error that arose during amplification or sequencing.

9. The method of claim 1, further comprising identifying a true mutation that is present in both strands of one of the double-stranded cfDNA molecules.

10. The method of claim 9, wherein the true mutation is identified when it is present in substantially all first-strand sequencing reads and second-strand sequencing reads for the double-stranded cfDNA molecule.

11. The method of claim 10, wherein the true mutation is identified when it is present in all first-strand sequencing reads and second-strand sequencing reads for the double-stranded cfDNA molecule.

12. The method of claim 1, wherein generating error-corrected sequences comprises comparing the first-strand sequencing reads with the second-strand sequencing reads within each of a plurality of groups of reads, wherein the groups of reads are distinguishable by the different pairs of cyphers.

13. The method of claim 1, wherein the cfDNA molecules are isolated from a blood sample of a subject.

14. The method of claim 1, wherein the cfDNA molecules are isolated from a subject having cancer.

15. The method of claim 1, further comprising detecting a cfDNA molecule from a cancer.

* * * * *

SEQUENCE LISTING

```
<160> NUMBER OF SEQ ID NOS: 8

<210> SEQ ID NO 1
<211> LENGTH: 7
<212> TYPE: DNA
<213> ORGANISM: Artificial Sequence
<220> FEATURE:
<223> OTHER INFORMATION: Random cypher sequence
<220> FEATURE:
<221> NAME/KEY: misc_feature
<222> LOCATION: (1)..(7)
```

<223> OTHER INFORMATION: n = A,T,C or G

<400> SEQUENCE: 1 nnnnnnn                                                                  7

<210> SEQ ID NO 2
<211> LENGTH: 195
<212> TYPE: DNA
<213> ORGANISM: Artificial Sequence
<220> FEATURE:
<223> OTHER INFORMATION: An oligonucleotide containing EcoRI and BamHI
      restriction enzyme sites, adapter sequences, indices, and random
      7-nucleotide barcodes flanking a SmaI restriction enzyme site
<220> FEATURE:
<221> NAME/KEY: misc_feature
<222> LOCATION: (1)..(195)
<223> OTHER INFORMATION: n = A,T,C or G

<400> SEQUENCE: 2
gatacaggat ccaatgatac ggcgaccacc gagatctaca ctagatcgcg cctccctcgc      60
gccatcagag atgtgtataa gagacagnnn nnnncccggg nnnnnnnctg tctcttatac     120
acatctctga gcgggctggc aaggcagacc gtaaggcgaa tctcgtatgc cgtcttctgc     180
ttggaattcg ataca                                                      195

<210> SEQ ID NO 3
<211> LENGTH: 22
<212> TYPE: DNA
<213> ORGANISM: Artificial Sequence
<220> FEATURE:
<223> OTHER INFORMATION: forward primer sequence

<400> SEQUENCE: 3
gatacaggat ccaatgatac gg                                               22

<210> SEQ ID NO 4
<211> LENGTH: 22
<212> TYPE: DNA
<213> ORGANISM: Artificial Sequence
<220> FEATURE:
<223> OTHER INFORMATION: reverse primer sequence

<400> SEQUENCE: 4
tgtatcgaat tccaagcaga ag                                               22

<210> SEQ ID NO 5
<211> LENGTH: 23
<212> TYPE: DNA
<213> ORGANISM: Artificial Sequence
<220> FEATURE:
<223> OTHER INFORMATION: forward primer sequence

<400> SEQUENCE: 5
tctgtctcct tcctcttcct aca                                              23

<210> SEQ ID NO 6
<211> LENGTH: 19
<212> TYPE: DNA
<213> ORGANISM: Artificial Sequence
<220> FEATURE:
<223> OTHER INFORMATION: reverse primer sequence

<400> SEQUENCE: 6
aaccagccct gtcgtctct                                                   19

```
<210> SEQ ID NO 7
<211> LENGTH: 20
<212> TYPE: DNA
<213> ORGANISM: Artificial Sequence
<220> FEATURE:
<223> OTHER INFORMATION: forward primer sequence

<400> SEQUENCE: 7
aatgatacgg cgaccaccga                                           20

<210> SEQ ID NO 8
<211> LENGTH: 21
<212> TYPE: DNA
<213> ORGANISM: Artificial Sequence
<220> FEATURE:
<223> OTHER INFORMATION: reverse primer sequence

<400> SEQUENCE: 8
caagcagaag acggcatacg a                                         21
```